United States Patent
Ho et al.

(10) Patent No.: US 10,654,943 B2
(45) Date of Patent: May 19, 2020

(54) TRI-SPECIFIC ANTIBODIES FOR HIV THERAPY

(71) Applicant: The Rockefeller University, New York, NY (US)

(72) Inventors: David Ho, Chappaqua, NY (US); Jian Yu, New York, NY (US); Xin Yao, New York, NY (US); Yaoxing Huang, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 15/579,280

(22) PCT Filed: Jun. 2, 2016

(86) PCT No.: PCT/US2016/035439
§ 371 (c)(1),
(2) Date: Dec. 4, 2017

(87) PCT Pub. No.: WO2016/196740
PCT Pub. Date: Dec. 8, 2016

(65) Prior Publication Data
US 2018/0179299 A1  Jun. 28, 2018

Related U.S. Application Data

(60) Provisional application No. 62/169,808, filed on Jun. 2, 2015.

(51) Int. Cl.
| | | |
|---|---|---|
| *C07K 16/46* | (2006.01) | |
| *C07K 16/10* | (2006.01) | |
| *A61P 31/18* | (2006.01) | |
| *A61K 39/00* | (2006.01) | |

(52) U.S. Cl.
CPC ........... *C07K 16/468* (2013.01); *A61P 31/18* (2018.01); *C07K 16/1063* (2013.01); *A61K 2039/505* (2013.01); *C07K 2317/21* (2013.01); *C07K 2317/24* (2013.01); *C07K 2317/31* (2013.01); *C07K 2317/34* (2013.01); *C07K 2317/52* (2013.01); *C07K 2317/565* (2013.01); *C07K 2317/76* (2013.01); *C07K 2317/90* (2013.01); *C07K 2319/00* (2013.01)

(58) Field of Classification Search
CPC .............. C07K 16/468; C07K 16/1063; C07K 2319/00; C07K 2317/565; C07K 2317/24; C07K 2317/21; C07K 2317/76; C07K 2317/31
See application file for complete search history.

(56) References Cited

U.S. PATENT DOCUMENTS

| | | | |
|---|---|---|---|
| 9,951,106 B2 * | 4/2018 | Guan | A61K 39/12 |
| 10,023,892 B2 * | 7/2018 | Wong | C12N 9/24 |
| 2012/0121597 A1 | 5/2012 | Ho et al. | |
| 2014/0248295 A1 | 9/2014 | Song et al. | |
| 2014/0271580 A1 | 9/2014 | Garry et al. | |

FOREIGN PATENT DOCUMENTS

| | | |
|---|---|---|
| WO | 2010/028796 A1 | 3/2010 |
| WO | 2014/089152 A1 | 6/2014 |

* cited by examiner

*Primary Examiner* — Jeffrey S Parkin
(74) *Attorney, Agent, or Firm* — Hodgson Russ LLP

(57) ABSTRACT

Provided are tri-specific fusion antibodies created to target multiple epitopes of the Human Immunodeficiency Virus (HIV). The fusion antibodies provide improved potency and breadth against HIV as compared to monospecific and bispecific antibodies, and additionally provide a high barrier against viral resistance. Also disclosed are pharmaceutical formulations and therapeutic methods utilizing such fusion proteins.

8 Claims, 24 Drawing Sheets

Specification includes a Sequence Listing.

Other TriSpec combinations

Tri1 : 128/07-151 (3GS)
Tri2: 128/07-1400 (3GS)
Tri3: 128/07-145 (3GS)
Tri4: 121/117-1400 (4GS)

Figure 16

| Antibody | IC$_{80}$ Median | IC$_{80}$ Coverage |
|---|---|---|
| 128/07-151 (3GS) | 0.041 | 98.3 |
| 128/07-1400 (3GS) | 0.069 | 98.3 |
| 128/07-145 (3GS) | 0.172 | 95.0 |
| 121/117-1400 (4GS) | 0.138 | 97.5 |

Figure 22

| Trispecific Antibody Name(s) | Antibody Subunit Name | CDR1 | CDR2 | CDR3 | CDR1 | CDR2 | CDR3 |
|---|---|---|---|---|---|---|---|
| VRC07/PGT128-PGT145 OR 128/07-145 (Figures 5, 6, 14, 15, 16, 18) OR PGT128/VRC07-PGT145 (Figure 7) | PGT128 Heavy Chain Knob PGT145VH | NSFWGWVR | SYWNRGWT | FGGEVLRYTDWPKPAWVDL | GNSFSNHD | MSHEGGKT | GSKHRLRDYFLYNEYGPNYEEWGDYLATLDV |
| | PGT128 Light Chain | GTSNNF | DVN | GSLVGNWDVI | | | |
| | VRC07 Heavy Chain HoleCross PGT145VL | ncpin | wmkprggavsyarqlqg | gkvctardynwdfeh | HSLQHSTGANY | LAT | MQGLHSPWT |
| | VRC07 Light Chain VLCH1 | qygs | sgst | qqyef | | | |
| VRC07/PGT128-10E8 (Figure 2) OR 07/128-10E8 (Figure 3) | PGT128 Heavy Chain Knob 10E8VH | NSFWGWVR | SYWNRGWT | FGGEVLRYTDWPKPAWVDL | gfdfdnaw | lapqegwsv | tgkvydfwsgppqeevfqd |
| | PGT128 Light Chain | GTSNNF | DVN | GSLVGNWDVI | | | |
| | VRC07 Heavy Chain HoleCross 10E8VL | ncpin | wmkprggavsyarqlqg | gkvctardynwdfeh | rgdslrshyas | gknnrps | ssrdksgsrfsv |
| | VRC07 Light Chain VLCH1 | qygs | sgst | qqyef | | | |
| VRC07/PGT128-PGT151 (Figure 8) OR 128/07-151 (Figures 3, 4, 11, 13-16) OR PGT128/VRC07-PGT151 (Figure 7, 17) OR Trispe1 (Figures 8-10) | PGT128 Heavy Chain Knob PGT151VH | NSFWGWVR | SYWNRGWT | FGGEVLRYTDWPKPAWVDL | DFPFSXYP | ISGDAWHY | ARMFQESGPPRLDRWSGRNYYYSGMDV |
| | PGT128 Light Chain | GTSNNF | DVN | GSLVGNWDVI | | | |
| | VRC07 Heavy Chain HoleCross PGT151VL | ncpin | wmkprggavsyarqlqg | gkvctardynwdfeh | ESLRQSNGKTS | EVS | MQSKQFPLT |
| | VRC07 Light Chain VLCH1 | qygs | sgst | qqyef | | | |

Figure 22, continued

| | | | | | | | |
|---|---|---|---|---|---|---|---|
| VRC07/PGT128-PGDM1400 OR PGT128/VRC07-PGDM1400 (Figure 7, 17, 21) OR 128/07-1400 (Figure 12, 14, 15, 16, 18) | PGT128 Heavy Chain Knob PGT145VH | NSFWGWVR | SYWNRGWT | FGGEVLRYTDMPKPAWVDL | GNTLKTYD | ISHEGDKK | CAKGSKHRLRDYALYDDDGALNWAVDYLSNLEFW |
| | PGT128 Light Chain | GTSNNF | DVN | GSLVGNWDVI | | | |
| | VRC07 Heavy Chain HoleCross PGT145VL | ncpln | wmkpntggavsyvardqg | glvctardynwdfeh | HSLIHGDRNNY | LAS | CMQGRESPWTF |
| | VRC07 Light Chain VLCH1 | dyef | sgst | qqyef | | | |
| PGT128/3BNC117-PGDM1400 (Figure 22) | PGT128 Heavy Chain Knob PGDM1400VH | NSFWGWVR | SYWNRGWT | FGGEVLRYTDMPKPAWVDL | GNTLKTYD | ISHEGDKK | CAKGSKHRLRDYALYDDDGALNWAVDYLSNLEFW |
| | PGT128 Light Chain | GTSNNF | DVN | GSLVGNWDVI | | | |
| | 3BNC117 Heavy Chain HoleCross 1400VL | DYFIH | WINPKTGQPNNPRQFQG | QRSDYWD | HSLIHGDRNNY | LAS | CMQGRESPWTF |
| | 3BNC117 Light Chain VLCH1 | QANGYLN | DGSKLER | QVYEF | | | |
| 121/117-1400 (Figures 14-16) OR PGT121/3BNC117-PGDM1400 (Figure 19) | PGT121 Heavy Chain Knob PGDM1400VH | GASISDSY | VHKSGDT | TLHGRRYGIVAFNEWFTYFYMDV | GNTLKTYD | ISHEGDKK | CAKGSKHRLRDYALYDDDGALNWAVDYLSNLEFW |
| | PGT121 Light Chain | SLGSRA | NNQ | HIWDSRVPTKWV | | | |
| | 3BNC117 Heavy Chain HoleCross PGDM1400VL | DYFIH | WINPKTGQPNNPRQFQG | QRSDYWD | HSLIHGDRNNY | LAS | CMQGRESPWTF |
| | 3BNC117 Light Chain VLCH1 | QANGYLN | DGSKLER | QVYEF | | | |

Figure 22, continued

| | | | | | | | | |
|---|---|---|---|---|---|---|---|---|
| PGT121/3BNC117-PGT151 (Figure 20) | PGT121 Heavy Chain Knob PGT151VH | GASISDSY | VHKSGDT | TLHGRRIYGIVAFNEWFTYFMDV | | | ISGDAWHV | ARMFQESGPPRLDRWSGRNYYYSGMDV |
| | PGT121 Light Chain | SLGSRA | NNQ | HIWDSRVPTKWV | | | | |
| | 3BNC117 Heavy Chain HoleCross PGT151VL | DYFIH | WINPKTGQPNNPRQFQG | QRSDYWD | | | EVS | MQSKDPPLT |
| | 3BNC117 Light Chain VLCH1 | QANGYLN | DGSKLER | QVYEF | | | | |
| | | | | | | | | |
| 151/07-128 (Figures 3-4) | PGT151 Heavy Chain Knob PGT128VH | DFPFSKYP | ISGDAWHV | ARMFQESGPPRLDRWSGRNYYYSGMDV | | | SYWNRGWT | FGGEVLRYTDWPKPAWVDL |
| | PGT151 Light Chain | ESLRQDSNGKTS | EVS | MQSKDPPLT | | | | |
| | VRC07 Heavy Chain HoleCross PGT128VL | nqpin | wmkprggavsyarqlqg | gkyctardyrwdfeh | | | DVN | GSLVGNWDVI |
| | VRC07 Light Chain VLCH1 | qygs | sgst | qqyef | | | | |
| | | | | | | | | |
| 10-1074/3BNC117-PGDM1400 (Figure 21) | 10-1074 Heavy Chain Knob PGDM1400VH | GDSMNNYY | ISDRESA | ATARRGQRWGVVSFGEFFYYSMDV | | | SHEGDKK | CAKGSKHRLRDYALYDDDGALNWAVDYLSNLEFW |
| | 1074 Light Chain | ALGSRA | NNQ | HIWDSRSGFSWS | | | | |
| | 3BNC117 Heavy Chain HoleCross 1400VL | DYFIH | WINPKTGQPNNPRQFQG | QRSDYWD | | | LAS | CMQGRESPWTF |
| | 3BNC117 Light Chain VLCH1 | QANGYLN | DGSKLER | QVYEF | | | | |

TRI-SPECIFIC ANTIBODIES FOR HIV THERAPY

CROSS REFERENCE TO RELATED APPLICATIONS

This application claims priority to U.S. patent application No. 62/169,808, filed Jun. 2, 2015, the disclosure of which is incorporated herein by reference.

STATEMENT REGARDING FEDERALLY FUNDED RESEARCH

This invention was made with government support under Grant No. DP1DA033263 awarded by the NIH. The government has certain rights in this invention.

FIELD OF THE DISCLOSURE

The disclosure provides tri-specific antibodies that target multiple epitopes of the Human Immunodeficiency Virus (HIV) virus. The tri-specific antibodies exhibit improved potency and breadth against HIV as compared to monospecific and bispecific antibodies, and additionally provide a high barrier against viral resistance that can be exhibited by HIV when targeted against one or a combination of monoclonal or bi-specific antibodies. Also disclosed are pharmaceutical formulations and therapeutic methods utilizing the tri-specific antibodies. The formulations and methods are useful for treating HIV infection in a subject, decreasing the viral load of HIV in a patient, and/or preventing the transmission of HIV to subjects.

BACKGROUND

Human antibodies to human immunodeficiency virus-1 (HIV-1) can neutralize a broad range of viral isolates in vitro and protect non-human primates against infection. However, it has been reported that these antibodies exert selective pressure on the virus and escape variants emerge within a short period of time. Since HIV-1 can escape from antibody monotherapy, combinations of broadly neutralizing antibodies (bNAb) have been studied and shown to effectively control HIV-1 infection and suppress viral load to levels below detection (Nature. 2012 Dec. 6; 492(7427):118-22). Although broadly neutralizing monoclonal antibodies (bNAbs) are considered to be a potential therapeutic option for the prophylaxis and treatment of HIV infection, their lack of breadth against all HIV variants has been one of the limiting factors. Further studies have reported that combinations of different bNAbs to generate bispecific HIV-1-neutralizing antibody (bibNAb) can provide sufficient neutralization breadth and potency against diverse viruses, including neutralization escape mutants (J Acquir Immune Defic Syndr. 2014 Aug. 15; 66(5):473-83). However, it also has been previously demonstrated that at least three different HIV antiretroviral small molecules are needed to effectively suppress HIV. This suggests that at least three different HIV targeting monoclonal antibodies would be required for long-term suppression of HIV. The present invention addresses problems of HIV-1 immunotherapy.

SUMMARY OF THE DISCLOSURE

Disclosed herein are tri-specific antibodies created to provide antigen-binding sites that target three distinct epitopes on the HIV envelope. The tri-specific fusion antibodies disclosed herein provide improved potency and breadth against HIV as compared to monospecific and bispecific antibodies, and additionally provide high barrier against viral resistance.

In some embodiments, the tri-specific fusion proteins assume the configuration of an intact IgG molecule directed to a first and second antigen (which can be any isotype, i.e., $IgG_1$, $IgG_2$, $IgG_3$, and $IgG_4$), connected via the CrossMAb methodology, and an antigen-binding domain of a third antibody directed to a third antigen via linkers at the C termini of the CrossMAb's heavy chains. We determined that linking the antigen binding domain of a third antibody directed to a third antigen at the N-terminus did not function.

In specific embodiments, the tri-specific fusion protein comprises three antigen-binding sites that target three distinct epitopes on the HIV envelope.

In additional embodiments, the Fc region of a tri-specific fusion protein has been engineered to provide a better PK profile, including improved stability and improved recycling capability.

The described invention provides a tri-specific fusion antibody, comprising three antigen-binding sites which bind to three distinct epitopes on the HIV envelope. These epitopes can be in any combination of the CD4 binding site, CD4 induced binding site, V1/V2, V2, V3, gp41, gp120/gp41 and gp120 domains, in the HIV envelope. In some embodiments, the tri-specific fusion antibody is a tri-specific fusion antibody comprising an intact anti-HIV envelope CrossMAb antibody or a fragment thereof which provides said first and second antigen-binding sites, conjugated to an anti-HIV envelope antibody or a fragment thereof which provides said third antigen-binding site. In some embodiments, the tri-specific fusion antibody is a tri-specific fusion antibody wherein said anti-HIV antibody is humanized or monkeynized. In some embodiments, the tri-specific fusion antibody is a tri-specific fusion antibody wherein the tri-specific antibody is additionally modified in the FcRn region to include one or more mutations that improve recycling of the tri-specific antibody. In some embodiments, the tri-specific fusion antibody is a tri-specific fusion antibody wherein the HIV-envelope antibody or fragment thereof is selected from an antibody contained within the tri-specific antibodies listed in Table 1. The described invention further provides a tri-specific fusion antibody comprising a first antigen-binding site which binds to an epitope on the HIV envelope, conjugated to a second antigen-binding site which binds to an second epitope on the HIV envelope; and a third antigen-binding site which binds to a third epitope on the HIV envelope. In some embodiments, the tri-specific fusion antibody is a tri-specific fusion antibody wherein the first antigen-binding site is from an anti-HIV antibody of Table 1. In some embodiments, the tri-specific fusion antibody is a tri-specific fusion antibody wherein the second antigen-binding site is from an anti-HIV antibody of Table 1. In some embodiments, the tri-specific fusion antibody is a tri-specific fusion antibody wherein the third antigen-binding site is from an anti-HIV antibody of Table 1. The described invention further provides methods of treating a subject infected with HIV comprising administering to the subject a therapeutically effective amount of the tri-specific fusion protein according to any one of the fusion proteins described herein. The described invention further provides methods of inhibiting HIV infection in a subject in need thereof comprising administering to the subject a therapeutically effective amount of the tri-specific protein according to any one of the proteins described herein. The described invention further provides methods of inhibiting a HIV-positive pregnant subject from transmitting HIV to the fetus and/or child, comprising administering to the subject and/or child a therapeutically effective amount of the tri-specific fusion protein according to any one of the fusion proteins described herein.

Pharmaceutical formulations and therapeutic methods utilizing the tri-specific proteins disclosed herein also are provided.

In certain and non-limiting embodiments, compositions and methods of this disclosure involve tri-specific antibodies selected from the group consisting of VRC07/PGT128-PGT145; VRC07/PGT128-10E8; VRC07/PGT128-PGT151; VRC07/PGT128-PGDM1400; PGT128/3BNC117-PGDM1400; PGT121/3BNC117-PGDM1400; PGT121/3BNC117-PGT151; 151/07-128, 0-1074/3BNC117-PGDM1400, and all combinations thereof.

BRIEF DESCRIPTION OF THE FIGURES

FIG. 16 provides a tabular summary of data presented in FIGS. 14 and 15 as a calculation of the potency and breadth of the four trispecific antibodies.

FIG. 22 provides CDR sequences for trispecific antibodies 1) VRC07/PGT128-PGT145; 2) VRC07/PGT128-10E8; 3) VRC07/PGT128-PGT151; 4) VRC07/PGT128-PGDM1400; 5) PGT128/3BNC117-PGDM1400; 6) PGT121/3BNC117-PGDM1400; 7) PGT121/3BNC117-PGT151; 8) 151/07-128; and 9) 10-1074/3BNC117-PGDM1400. FIG. 22 also provides alternative names for these trispecific antibodies that are used from time to time in this disclosure. The CDR sequences in FIG. 22 are also provided in the accompanying sequence listing that forms a part of this disclosure.

DETAILED DESCRIPTION

Figure 1:
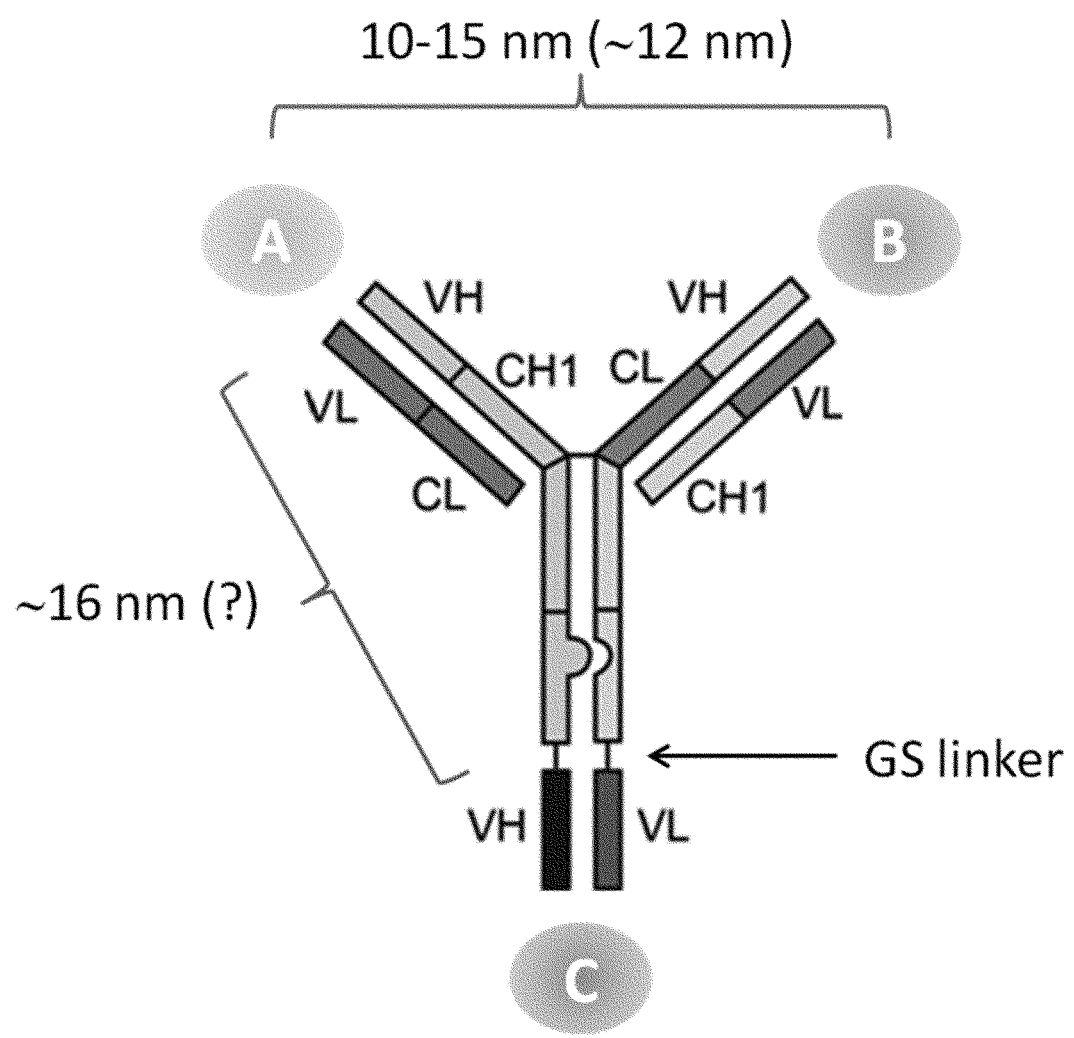
FIG. 1 shows an illustrative diagram of a Tri-specific antibody.

The present invention provides fusion antibodies created to include three different HIV epitopes into one antibody-like molecule (a "tri-specific fusion antibody"). These different HIV epitopes can include, but are not limited to, the CD4 binding site, CD4 induced binding site, V1/V2 region, V2 region, V3 region, gp41, gp120/gp41 interface and gp120 domain, or fragments thereof. The tri-specific fusion antibodies provide improved potency and breadth against HIV as compared to monospecific and bispecific antibodies. Such fusion antibodies also provide a high barrier against development of viral resistance. For example, it is demonstrated in the present disclosure that certain of the instant trispecific antibodies can neutralize up to 100% of 118 pseudotyped viruses that are present in an HIV panel that is used to test neutralization efficacy. Thus, it is considered that trispecifc antibodies of this disclosure can be used to overcome, for example, preexisting resistance of HIV to monospecific and bispecific anti-HIV antibodies that are directed to the same epitopes as the trispecific antibodies described herein. It is accordingly expected that trispecific antibodies of this disclosure will be effective in overcoming resistance that may develop by mutations in any one of the three particular epitopes that are targeted by the trispecific antibodies The basic structure of the fusion proteins disclosed herein is typically a whole IgG-like molecule containing a first and second antigen-binding site directed to a first and second antigen via the CrossMAb methodology, and third antigen-binding site created through the dimerization of a variable heavy chain domain and a variable light chain domain that are each genetically linked to the C-termini of the heavy chains of the first and second antigen binding domains (see FIG. 1). Tri-specific antibodies display an HIV neutralization activity with good potency and breadth against HIV, and at a similar potency and breadth to that of the three parental monoclonal antibodies administered as a mixture. However, the trispecific antibody allows for this neutralization activity in one molecule, instead of three, and at a lower molar quantity of total antibody. Data indicates that the pharmacokinetics of this trispecific antibody in mice can be similar to that of traditional monoclonal antibodies, and the HIV envelope targeting tri-specific antibody is expected to allow for FcR binding and antibody-dependent cellular cytotoxicity (ADCC) in vitro and in vivo.

The features and applications of these trispecific fusion antibodies are described further below.

Definitions

An "antigen" refers to a molecule which contains one or more epitopes and which is capable of eliciting an immunological response. "Antigenic molecules" are also used in a general sense to refer to molecules that are binding targets of the fusion proteins disclosed herein.

An "epitope", also known as antigenic determinant, is the portion of an antigenic molecule or molecules that is recognized by the immune system, i.e., B cells, T cells or antibodies. An epitope can be a conformational epitope or a linear epitope. A conformational epitope is formed by discontinuous sections of an antigenic molecule, or formed by multiple molecules. In the case where the antigen is a protein, a conformational epitope can be formed by discontinuous amino acid residues of the same protein molecule, or by amino acid residues on different molecules of the protein (e.g., a quaternary epitope formed by a multimer of the protein). A linear epitope is formed by continuous sections of an antigen, e.g., a continuous sequence of amino acids of a protein antigen.

The term "antibody" is used herein broadly and encompasses intact antibody molecules, which include intact polyclonal, monoclonal, monospecific, polyspecific, chimeric, humanized, human, primatized, single-chain, single-domain, synthetic and recombinant antibodies, and antibody fragments that have a desired activity or function.

The term "chimeric antibody" refers to antibodies containing polypeptides from different sources, e.g., different species or different antibody class or subclass. Examples of chimeric antibodies include an antigen-binding portion of a murine monoclonal antibody fused an Fc fragment of a human immunoglobulin. Methods for making chimeric antibodies are known in the art.

The term "humanized antibody" refers to antibodies that contain non-human sequence elements in a human immunoglobulin backbone or framework. Generally, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having a desired specificity, affinity and capacity. In some instances, framework region (FR) residues of the human immunoglobulin are also replaced by non-human residues. Humanized antibodies may also, in some instances, contain residues that are not found in either the recipient antibody or the donor antibody and introduced to further refine antibody performance. In general, a humanized antibody contains substantially all of at least one, and typically two, variable domains, in which all or substantially all of the hypervariable regions correspond to those of a non-human immunoglobulin and all or substantially all of the framework regions are those of a human immunoglobulin sequence. A humanized antibody optionally also contains at least a portion of an immunoglobulin constant region (Fc), typically that of a human immunoglobulin. Methods for making humanized antibodies are documented in the art.

The term "primatized antibody" refers to antibodies that contain non-primate sequence elements in a primate immunoglobulin backbone or framework. For example, primatized antibodies can be made from a primate immunoglobulin (recipient antibody) by replacing residues in a hypervariable region (CDRs) of the recipient antibody with residues from a hypervariable region of a donor antibody from a non-primate species such as mouse, rat, rabbit or nonhuman primate having a desired specificity, affinity and capacity. Alternatively, primatized antibodies can be made suitable for administration to a desirable primate species by using a recipient immunoglobulin having non-primate sequences or sequences from a different primate species and introducing the Fc fragment, and/or residues, including particularly framework region residues, from the desirable primate, into the recipient immunoglobulin. Examples of primatized antibodies include "monkeynized" antibodies disclosed herein in the Examples section.

The term "monospecific antibody" refers to antibodies that recognize and bind to one epitope.

The term "polyspecific antibody" refers to antibodies formed from at least two separate antibodies and binding to multiple (i.e., two or more) separate epitopes.

As described above, the term "antibody" also includes fragments of an intact antibody, or "antibody fragments", including particularly antigen-binding fragments of an intact antibody. Examples of antigen-binding fragments include, but are not limited to, Fab fragments (consisting of the VL, VH, CL and CH1 domains), Fab' fragments (which differs from Fab fragments by having an additional few residues at the C-terminus of the CH1 domain including one or more cysteines from the antibody hinge region), (Fab').sub.2 fragments (formed by two Fab' fragments linked by a disulphide bridge at the hinge region), Fd fragments (consisting of the VH and CH1 domains), Fv fragments (referring to a dimer of one heavy and one light chain variable domain in tight, non-covalent association which contains a complete antigen recognition and binding site), dAb fragments (consisting of a VH domain), single domain fragments (VH domain, VL domain, VHH domain, or VNAR domain), isolated CDR regions, scFv (or "single chain Fv", referring to a fusion of the VL and VH domains, linked together via a linker), and other antibody fragments that retain antigen-binding function.

The term "CDR" or "complementarity determining region" refers to the hypervariable regions within the variable domain of an antibody. There are 3 CDRs in each of the heavy chain and light chain variable domains, and are composed of amino acid residues responsible for antigen-binding. The term "framework region" or "FR" refers to the more conserved portions of the variable domains and is composed of residues other than the hypervariable region residues.

The term "antigen-binding site" of an antibody means a conformation and/or configuration formed by amino acids of the antibody to which an antigen binds. For example, the three CDRs of each of the VH and VL domains interact to define an antigen-binding site on the surface of the VH-VL dimer. Together, the six CDRs confer antigen-binding specificity to the antibody. It should be noted, however, a single variable domain (i.e., VH or VL) can also recognize and bind antigen, albeit often less effectively than the whole binding site with all six CDRs.

The term "neutralizing antibody" refers to an antibody that inhibits, reduces or completely prevents HIV-1 infection. Whether an antibody is a neutralizing antibody can be determined by in vitro assays described in the Examples section below.

The term "potent neutralizing antibody" refers to an antibody which, when used at a low concentration, reduces HIV-1 infection by at least 50%, 60%, 70%, 80%, 90%, 95%, 99% or greater. Concentrations below 50 ug/ml, between 1 and 50 ug/ml, or even below 1 ug/ml, are considered "low concentrations". In some embodiments, low concentrations are concentrations in the picomolar range, such as 10-900 ng/ml, and include any concentration in that range, such as 800, 700, 600, 500, 400, 300, 200, 100, 75, 50, 25, 10 ng/ml, or even less than 10 ng/ml.

The term "broad neutralizing antibody" refers to an antibody which inhibits HIV-1 infection, as defined by a 50% inhibition of infection in vitro, in more than 50%, 60%, 70%, 80%, 90%, 95%, 99% or greater, of a large panel of (greater than 100) HIV-1 envelope pseudotyped viruses and viral isolates.

The term "fragment" as used herein refers to a physically contiguous portion of the primary structure of a biomolecule. In the case of proteins, a fragment may be defined by a contiguous portion of the amino acid sequence of a protein and may be at least 3-5 amino acids, at least 6-10 amino acids, at least 11-15 amino acids, at least 16-24 amino acids, at least 25-30 amino acids, at least 30-45 amino acids and up to the full length of the protein minus a few amino acids. In the case of polynucleotides, a fragment is defined by a contiguous portion of the nucleic acid sequence of a polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

A "fusion protein" refers to two or more peptides of different origins connected to each other via a linker or linkers. For example, a fusion protein can include a protein conjugated to an antibody. Other examples include, an antibody conjugated to a different antibody or an antibody conjugated to a Fab fragment. The Fab fragment can be conjugated to the N terminus or C terminus of the heavy or light chain of the antibody, or other regions within the antibody. The term fusion protein and fusion construct are used herein interchangeably.

A "peptide" is any compound formed by the linkage of two or more amino acids by amide (peptide) bonds, usually a polymer of alpha-amino acids in which the alpha-amino group of each amino acid residue (except the NH2 terminus) is linked to the alpha-carboxyl group of the next residue in a linear chain. The terms peptide, polypeptide and poly (amino acid) are used synonymously herein to refer to this class of compounds without restriction as to size, unless indicated to the contrary. Members of this class having a large size are also referred to as proteins and include antibodies.

The term "linker" refers to a chemical moiety that connects one peptide to another, e.g., one antibody to another. Linkers can also be used to attach antibodies to labels or solid substrates. A linker can include amino acids. Linkers can be straight or branched, saturated or unsaturated carbon chains. They can also include one or more heteroatoms within the chain or at the termini of the chains. By "heteroatoms" is meant atoms other than carbon which are chosen from the group comprising of oxygen, nitrogen, sulfur, phosphorus, boron and halogen. In specific embodiments, linkers are peptides. The use of a linker may or may not be advantageous or needed, depending on the specific antibody pairs. Methods and techniques for the attachment of a linker to an antibody are known in the art.

Fusion Antibody Targeting Multiple HIV Epitopes

The described invention is directed to tri-specific fusion antibodies that contain three different HIV antigen-binding sites in one antibody-like molecule (a "trispecific fusion antibody"). The epitopes typically include the CD4 binding site, CD4 induced binding site, V1/V2 region, V2 region, V3 region, gp41, gp120/gp41 interface or gp120 domain that target the HIV envelope. Fusion antibodies having specificities towards simply three different antigens are also referred to herein as "tri-specific antibodies." Tri-specific fusion antibodies can be modified to include additional antigen binding sites to provide other polyspecific antibodies. For example, a tri-specific fusion antibody includes different HIV targeting epitopes such as the CD4 binding site, CD4 induced binding site, V1/V2 region, V2 region, V3 region, gp41, gp120/gp41 interface or gp120 domain.

To make the tri-specific fusion antibodies, we synthesized multiple codon optimized variable heavy chain and variable light chain genes that each targeted a unique epitope on the HIV envelope. The first and second antigen binding sites can be engineered using the CrossMAb methodology (see, for example, Proc Natl Acad Sci USA. 2011 Jul. 5; 108(27): 11187-92, incorporated herein by reference in its entirety). For the CrossMab portion of the molecules, one heavy chain targeting epitope A with the hole and cross mutation was synthesized. A second heavy chain targeting epitope B with the knob mutation also was synthesized to ensure efficient heterodimerization of these two distinct heavy chains via the knob-in-hole pairing. To ensure efficient light chain pairings with the appropriate heavy chain partners, one light chain targeting epitope A with the cross mutation was synthesized and one light chain targeting epitope B was synthesized. To create trispecificity in these molecules, a variable light chain gene targeting epitope C was genetically linked to the C-terminus of the heavy chain hole gene with a 3× GS linker, and a variable heavy chain gene targeting epitope C was genetically linked to the C-terminus of the heavy chain knob gene with a 3× GS linker. Additionally, linkers of different lengths can be used such as, but not limited to, 2× GS linkers and 4× GS linkers, to 50× GS linkers. Thus, when the two distinct heavy chains of the CrossMab form a heterodimer, it brings together the variable heavy and light chain domains of the epitope C-targeting moiety that functions as a third HIV neutralizing moiety.

Each codon optimized gene mentioned above was synthesized and cloned into a plasmid vector to generate a total of four plasmids per trispecific antibody. To produce the antibody, the four plasmids were transfected into 293 cells, and the resulting trispecific antibody produced was purified on a Protein A column for use in functional characterization experiments.

Generally speaking, the structure of the fusion proteins disclosed herein is composed of an intact IgG-like molecule containing a first and second antigen-binding site directed to a first and second antigen via the CrossMAb methodology, and a third antigen-binding site created through the dimerization of a variable heavy chain domain and a variable light chain domain that are each genetically linked to the C-termini of the variable heavy chains of the first and second antigen binding domains. For example, a fusion antibody having tri-specificities towards HIV can be formed by conjugating an intact CrossMab antibody with two antigen-binding fragments of two separate anti-HIV antibodies, and a third antigen-binding site created through the dimerization of a variable heavy chain domain and a variable light chain domain that are each genetically linked to the C-termini of the heavy chains of the first and second antigen binding domains. Alternately, a fusion antibody having tri-specificities can be formed by conjugating 3 antigen-binding fragments of 3 separate anti-HIV antibodies. In each of these scenarios, a tri-specific fusion antibody contain antigen-binding sites that bind to any combination of epitopes on the HIV envelope or any combination thereof (see Example 1, Example 2 for non-limiting illustrations).

Anti-HIV Env antibodies have been described in the art and can also be readily generated by those skilled in the art. The env gene encodes a precursor protein, gp160. During HIV reproduction, the endogenous enzymes of the host cell cleave gp160 into gp120 and gp41. Illustrative and specific examples of tri-specific anti-HIV Env antibodies are shown in Table 1.

In some embodiments, anti-HIV antibodies used herein in forming a tri-specific fusion antibody are directed to an epitope on an envelope protein of HIV, e.g., gp120 monomer or trimer, or gp41. Examples of anti-HIV antibodies suitable for use herein include, but are not limited to, VRC07, PGT128, 10E8, PGT151, PGT145, PGDM1400, 3BNC117, and PGT121. In some embodiments, a fusion antibody having tri-specificities towards the HIV envelope is composed of a CrossMAb antibody, conjugated with (i.e., covalently linked to) an antigen-binding fragment of a third distinct anti-HIV antibody or fragments thereof. As defined above, an antigen-binding fragment of anti-HIV antibody including Fab fragments, Fab' fragments, (Fab')$_2$ fragments, Fd fragments, Fv fragments, dAb fragments, single domain fragments, isolated CDR regions, scFvs, and other antibody fragments that retain HIV-binding function of an anti-HIV antibody. The antigen-binding fragments are fused to the C-termini of the heavy chains of the CrossMAb antibody. In some embodiments, the antigen-binding fragment is a single chain of the VH domain linked to the C-terminus of the heavy chain domain of a relevant anti-HIV antibody; while in other embodiments, the antigen-binding fragment is a single chain of the VL domain linked to the C-terminus of the heavy chain domain of a relevant anti-HIV antibody. Alternately, the tri-specific fusion antibody can contain three antigen-binding fragments of an anti-HIV antibody.

The linkage between the three antibody components, i.e., between the three distinct anti-HIV antibody portions, and/or between the VH and/or VL domains of an antigen-binding fragment, may be achieved by a peptide linker. The length of a linker is generally in the range of 5 to 50 amino acids, and in specific embodiments, in the range of 9-25 amino acids, such as 9, 12, 16, 20 or 24 amino acids. The linkers can be synthetic or native human antibody-derived sequences, or a combination of both. Generally speaking, the linkers are principally composed of relatively small, neutral amino acids, such as Glycine, Serine, Alanine, and can include multiple copies of a sequence enriched in Glycine and Serine, such as multiple copies of GGGGS (SEQ ID NO:54).

The tri-specific fusion antibodies disclosed herein can be produced by utilizing techniques available to those skilled in the art. For example, DNA molecules encoding a desirable tri-specific fusion antibody can be constructed based on the coding sequence of the three antibody components of the fusion using molecular cloning techniques. The resulting DNAs can be placed into expression vectors which are then transfected into host cells such as *E. coli* cells, simian COS cells, Chinese Hamster Ovary (CHO) cells, human embryonic kidney 293 cells, or myeloma cells including murine myeloma cells that do not otherwise produce immunoglobulin protein, to obtain the synthesis of monoclonal antibodies in the recombinant host cells.

Figure 7:
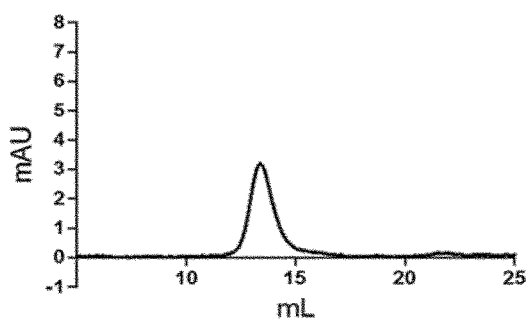
FIG. 7 shows SEC analysis of tri-specific antibodies.
Figure 7:
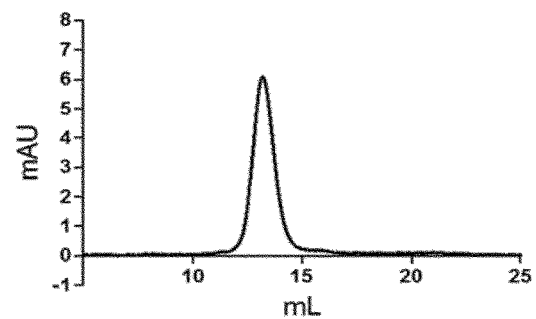
Figure 7:
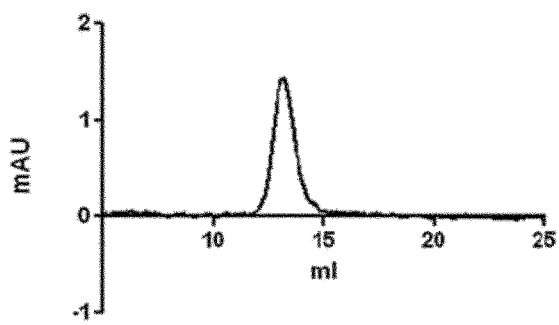
Figure 8:
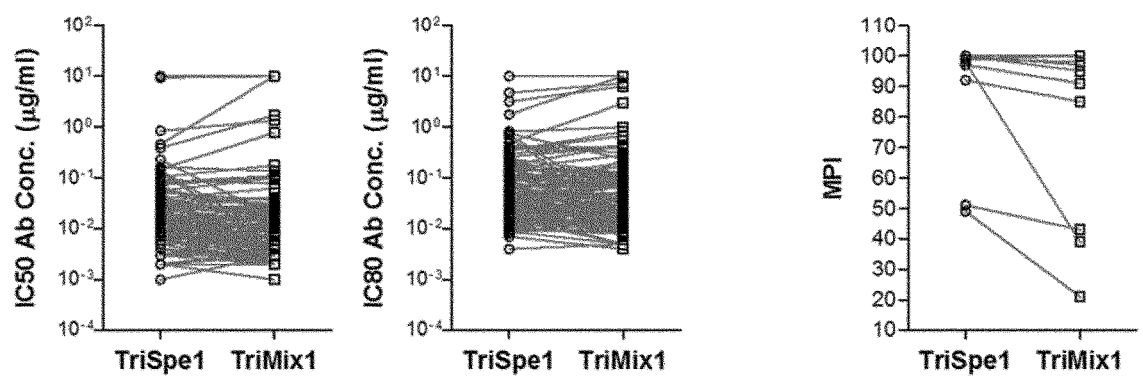
FIG. 8 shows Tri-specific fusion antibody vs Tri Mix neutralizing activity in vitro on a panel of 118 multi-clade viruses. TriSpe1 was tested up to 10 ug/ml (57 nm, VRC07/PGT128-PGT151); TriMix1 was tested up to 10 ug/ml each, 30 ug/ml total (200 nM) (VRC07+PGT128+PGT151)
Figure 20:
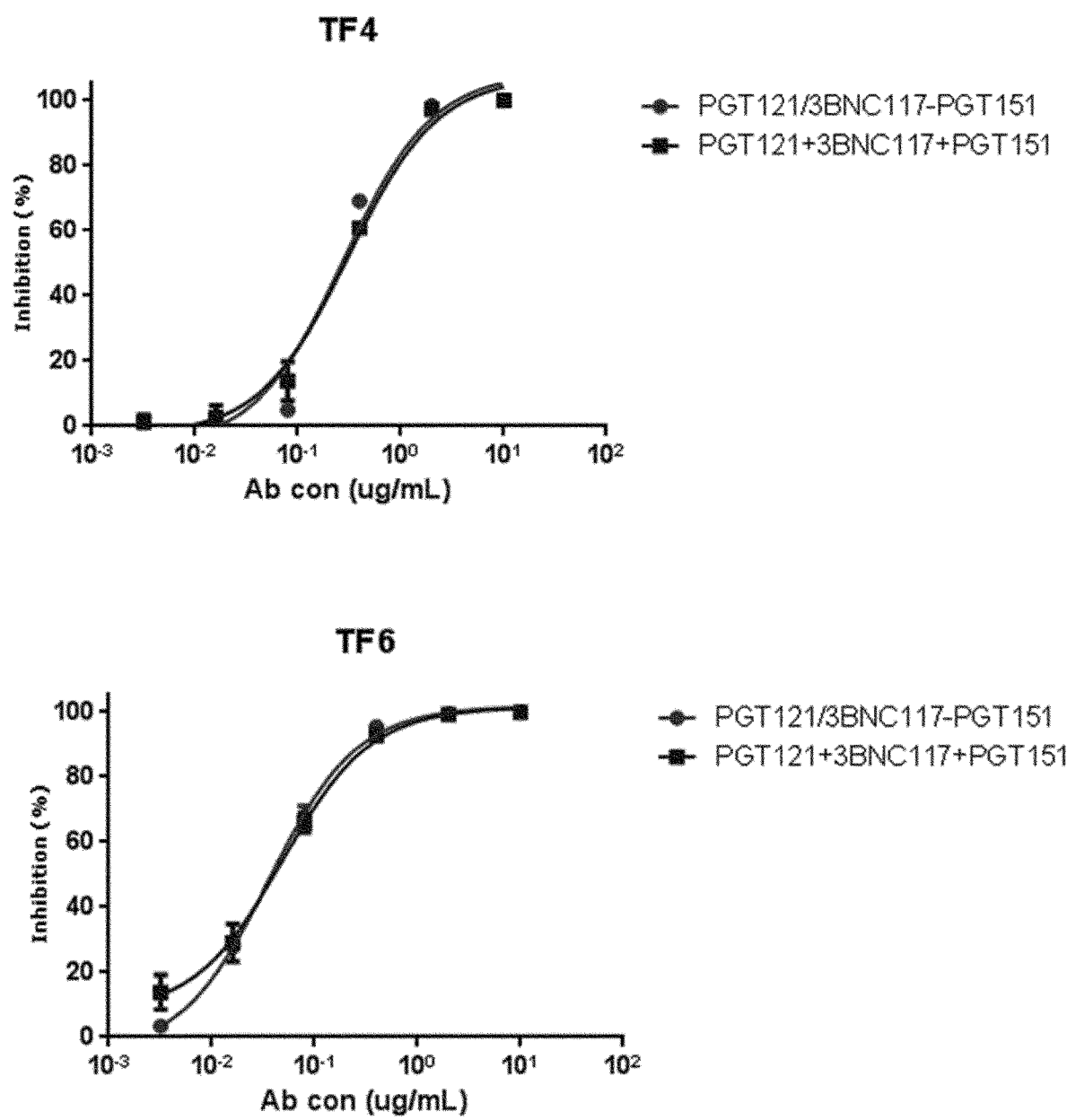
FIG. 20 provides results from analysis of an additional trispecific antibody comprised of the PGT121, 3BNC117 and PGT151 antibody moieties in a single molecule.
Figure 21:
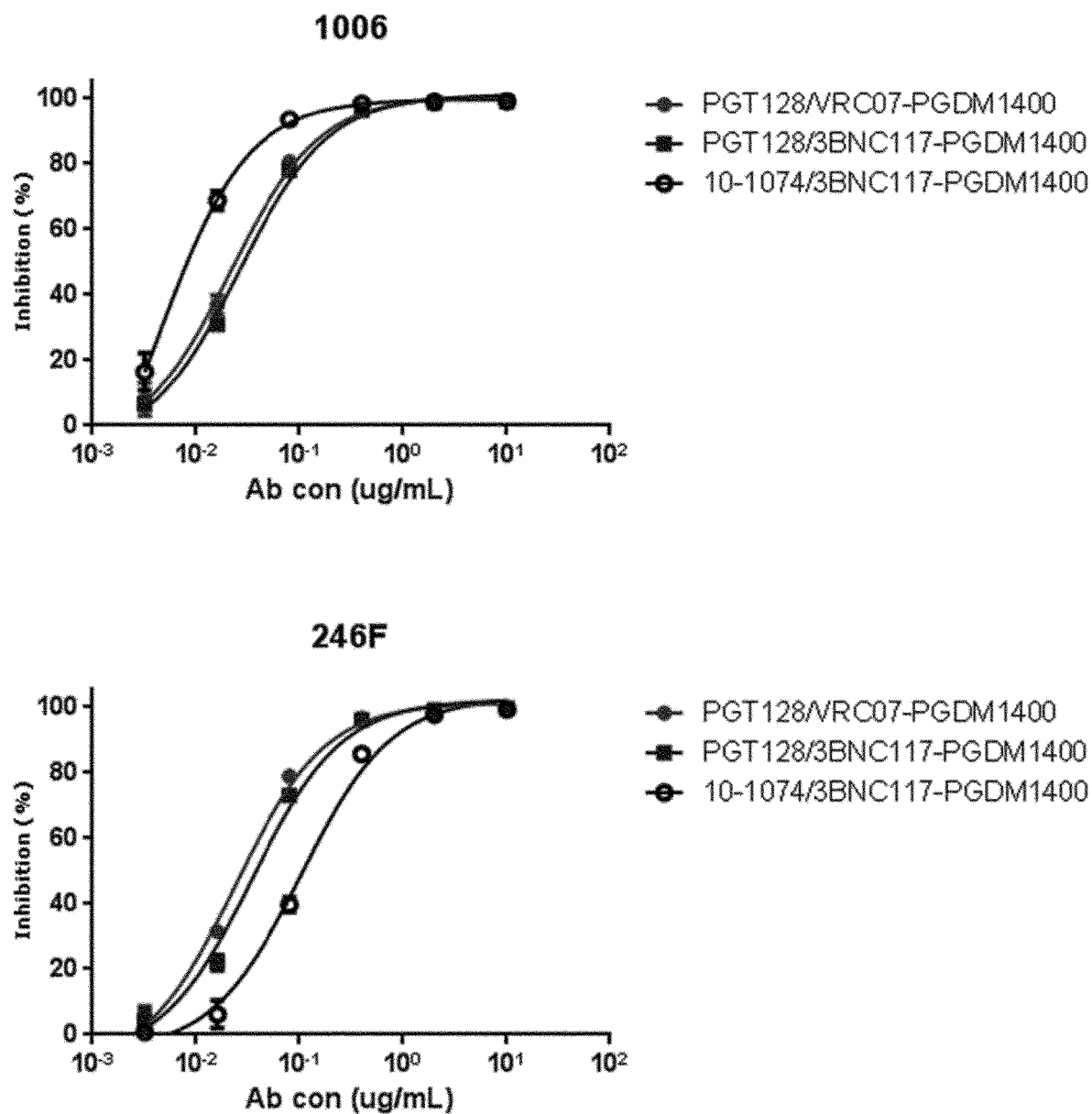
FIG. 21 provides an analysis of two additional trispecifics comprising 1) the PGT128, 3BNC117 and PDGM1400 antibody moieties in a single molecule, and 2) the 10-1074, 3BNC117, PGDM1400 antibody moieties in a single molecule.

As discussed above, trispecific antibodies of this disclosure can include CDR segments from the variable heavy (VH) and variable light (VL) chains from anti-HIV antibodies VRC07, PGT128, 10E8, PGT151, PGT145, PGDM1400, 3BNC117, PGT121 and 10-1074. The disclosure accordingly includes trispecific antibodies that each comprise six variable segments, three of which comprise VH chains, and three of which are VL chains. The three VH chains in each trispecific antibody of this disclosure comprise sets of three CDR1, CDR2 and CDR3 sequences selected from the VH CDR1, CDR2 and CDR3 sequences of the VRC07, PGT128, 10E8, PGT151, PGT145, PGDM1400, 3BNC117, PGT121 and 10-1074 antibodies. Likewise, the three VL chains in each trispecific antibody comprise sets of three CDR1, CDR2 and CDR3 sequences selected from the VL CDR1, CDR2 and CDR3 sequences of the VRC07, PGT128, 10E8, PGT151, PGT145, PGDM1400, 3BNC117, PGT121 and 10-1074 antibodies. The CDR sequences are provided in FIG. 22, which also provides in the "Trispecific Antibody Name(s)" column alternative nomenclature for the aforementioned antibodies that are used from time to time in the instant specification and figures. In non-limiting embodiments the present disclosure provides demonstrations of nine distinct trispecific antibodies described herein, sequences for which are described herein and presented in FIG. 22, as:

1) VRC07/PGT128-PGT145, also referred to as 128/07-145 (see, FIGS. 5, 6, 14, 15, 20, 22) or PGT128/VRC07-PGT145 (see FIG. 7);
2) VRC07/PGT128-10E8 (see, FIG. 2), also referred to as 07/128-10E8 (see, FIG. 2, upper right panel);
3) VRC07/PGT128-PGT151 (see, FIG. 8), also referred to as 128/07-151 (see, FIGS. 3, 4, 11, 13-16), also referred to as PGT128/VRC07-PGT151 (see, FIGS. 7 and 17) or TriSpe1 (see, FIGS. 8-10);
4) VRC07/PGT128-PGDM1400, also referred to as PGT128/VRC07-PGDM1400 (see, FIGS. 17 and 21), also referred to as 128/07-1400 (see, FIGS. 12, 14, 15, 16, and 18);
5) PGT128/3BNC117-PGDM1400 (see, FIG. 21);
6) PGT121/3BNC117-PGDM1400 (see, FIG. 19), also referred to as 121/117-1400 (see, FIGS. 14-16);
7) PGT121/3BNC117-PGT151 (see, FIG. 20);
8) 151/07-128 (see, FIGS. 3 and 4); and
9) 10-1074/3BNC117-PGDM1400 (see, FIG. 21).

As discussed above, the trispecific antibodies of this disclosure include a CrossMab portion comprising one heavy chain targeting epitope A with so-called hole mutation and a second heavy chain targeting epitope B with a so-called knob mutation. To facilitate efficient light chain pairings with the appropriate heavy chain partners, one light chain targeting epitope A with the cross mutation was synthesized and one light chain targeting epitope B was synthesized. To create trispecificity, a variable light chain gene targeting epitope C was genetically linked to the C-terminus of the heavy chain hole gene with a GS linker, and a variable heavy chain gene targeting epitope C was genetically linked to the C-terminus of the heavy chain knob gene with a GS linker. In another embodiment, a variable heavy chain gene targeting epitope C can be genetically linked to the C-terminus of the heavy chain hole gene with a GS linker, and a variable light chain gene targeting epitope C can be genetically linked to the C-terminus of the heavy chain knob gene with a GS linker.

CDR sequences of the representative nine trispecific antibodies discussed above are provided in FIG. 22, and below. FIG. 22 provides in the leftmost column indications of Figures where the particular trispecific antibody names are used. Sequence identifiers for unique antibody subunit CDRs as provided in FIG. 22 are as follows (there is no significance as between upper and lower case in the amino acid sequences of FIG. 22 or in this detailed description):

NSFWGWVR     SEQ ID NO: 1

SYWNRGWT     SEQ ID NO: 2

FGGEVLRYTDWPKPAWVDL     SEQ ID NO: 3

GNSFSNHD     SEQ ID NO: 4

MSHEGDKT     SEQ ID NO: 5

GSKHRLRDYFLYNEYGPNYEEWGDYLATLDV     SEQ ID NO: 6

GTSNNF     SEQ ID NO: 7

DVN     SEQ ID NO: 8

NCPIN     SEQ ID NO: 9

WMKPRGGAVSYARQLQG     SEQ ID NO: 10

GKYCTARDYYNWDFEH     SEQ ID NO: 11

HSLQHSTGANY     SEQ ID NO: 12

LAT     SEQ ID NO: 13

MQGLHSPWT     SEQ ID NO: 14

GFDFDNAW     SEQ ID NO: 15

ITGPGEGWSV     SEQ ID NO: 16

TGKYYDFWSGYPPGEEYFQD     SEQ ID NO: 17

RGDSLRSHYAS     SEQ ID NO: 18

GKNNRPS     SEQ ID NO: 19

SSRDKSGSRLSV     SEQ ID NO: 20

DFPFSKYP     SEQ ID NO: 21

-continued

ISGDAWHV     SEQ ID NO: 22

ARMFQESGPPRLDRWSGRNYYYYSGMDV     SEQ ID NO: 23

ESLRQSNGKTS     SEQ ID NO: 24

EVS     SEQ ID NO: 25

MQSKDFPLT     SEQ ID NO: 26

QYGS     SEQ ID NO: 27

SGST     SEQ ID NO: 28

QQYEF     SEQ ID NO: 29

GNTLKTYD     SEQ ID NO: 30

ISHEGDKK     SEQ ID NO: 31

CAKGSKHRLRDYALYDDDGALNWAVDVDYLSNLEFW     SEQ ID NO: 32

GASISDSY     SEQ ID NO: 33

VHKSGDT     SEQ ID NO: 34

TLHGRRIYGIVAFNEWFTYFYMDV     SEQ ID NO: 35

SLGSRA     SEQ ID NO: 36

NNQ     SEQ ID NO: 37

HIWDSRVPTKWV     SEQ ID NO: 38

DYFIH     SEQ ID NO: 39

WINPKTGQPNNPRQFQG     SEQ ID NO: 40

QRSDYWD     SEQ ID NO: 41

HSLIHGDRNNY     SEQ ID NO: 42

LAS     SEQ ID NO: 43

CMQGRESPWTF     SEQ ID NO: 44

QANGYLN     SEQ ID NO: 45

DGSKLER     SEQ ID NO: 46

QVYEF     SEQ ID NO: 47

GDSMNNYY     SEQ ID NO: 48

```
                                            SEQ ID NO: 49
ISDRESA

SEQ ID NO: 50
ATARRGQRIYGVVSFGEFFYYYSMDV

SEQ ID NO: 51
ALGSRA

SEQ ID NO: 52
HMWDSRSGFSWS

SEQ ID NO: 53
GSLVGNWDVI
```

Figure 2:
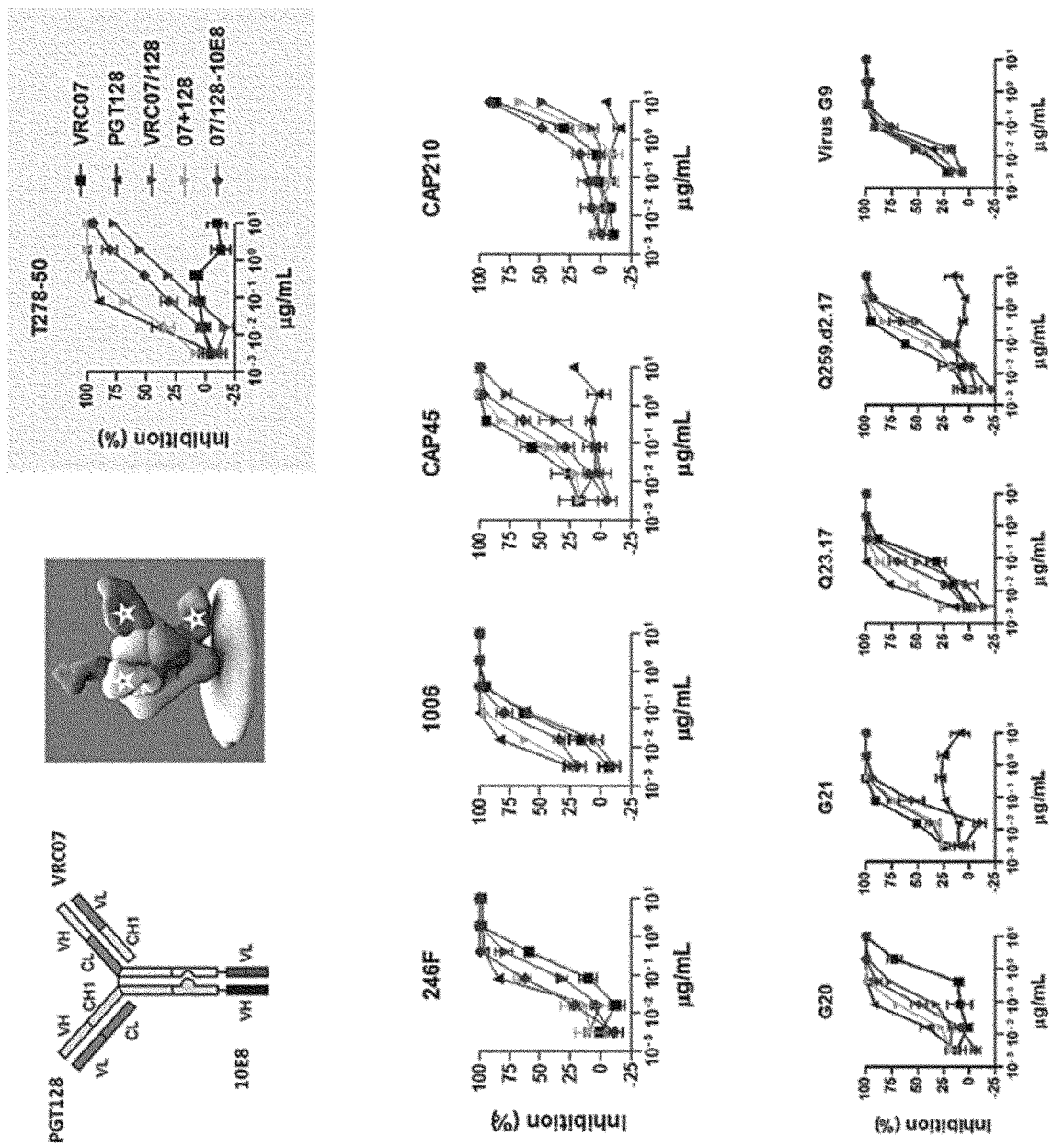
FIG. 2 shows a tri-specific antibody containing the PGT128, VRC07 and 10E8 antibody domains, which target the V3, CD4 binding site and gp41 domains, respectively, on the HIV envelope and its activity.
Figure 3:
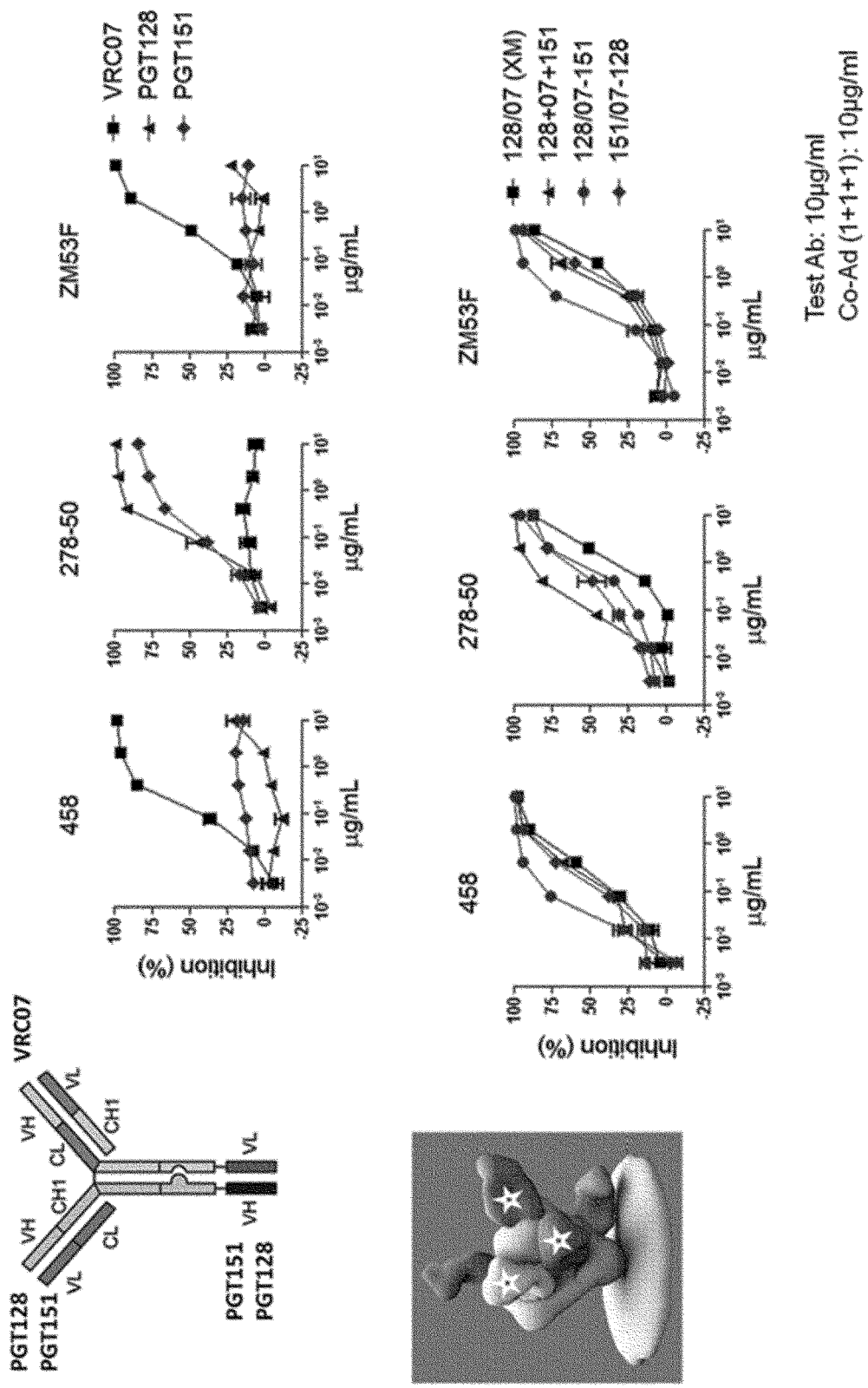
FIG. 3 shows two versions of tri-specific antibodies generated that contained the PGT128, VRC07 and PGT151 antibody domains, which target the V3, CD4 binding site and gp120/41 domains, respectively, on the HIV envelope and their activity.

By way of non-limiting illustration, one embodiment of this disclosure is exemplified by the trispecific antibody termed "VRC07/PGT128-10E8" which is illustrated in FIG. 2.

The CDR sequences for the VH and VL chains are given in the row of FIG. 22 having the VRC07/PGT128-10E8 term in the Trispecific Antibody Name(s) column, and is the second trispecific from the top. The sequences are provided starting at the top of the arms of the antibody and are accordingly shown in the N→C terminal orientation. As can be seen from FIG. 22 the "PGT128 Heavy Chain Knob 10E8VH" CDR sequences start at the left arm of the heavy chain variable region segment (VH) and are from the PGT128 antibody and are: SEQ ID NO:1—NSFWGWVR (CDR1), SEQ ID NO:2—SYWNRGWT (CDR2) and SEQ ID NO:3—FGGEVLRYTDWPKPAWVDL (CDR3). Continuing in the N→C terminal orientation in the heavy chain segment of the left arm in the illustration, and as shown in the VRC07/PGT128-10E8 sequence in FIG. 22, the second set of VH CDRs are from the 10E8 antibody, and have the 10E8 VH CDR sequences SEQ ID NO:15 gfdfdnaw (CDR1), SEQ ID NO:16—itgpgegwsv (CDR2) and SEQ ID NO:17—tgkyydfwsgyppgeeyfqd (CDR3).

Turning to the light chain VL sequences of the left arm of the VRC07/PGT128-10E8 construct, they are comprised of the CDR VL sequences from the PGT128 antibody (PGT128 Light Chain) and as shown in FIG. 22 are: SEQ ID NO:7—GTSNNF (CDR1), SEQ ID NO:8—DVN (CDR2) and SEQ ID NO:53—GSLVGNWDVI (CDR3).

Turning to the "right arm" of the VRC07/PGT128-10E8 construct, the heavy chain (VH) VRC07 sequences beginning at the top of the right heavy chain arm (Heavy Chain HoleCross 10E8VL) are: SEQ ID NO:9—ncpin (CDR1), SEQ ID NO:10—wmkprggaysyarqlqg (CDR2), and SEQ ID NO:11—gkyctardyynwdfeh (CDR3). Continuing in the N→C terminal orientation, which in the case of the VRC07/PGT128-10E8 construct comprises a set of VL CDRs from the 10E8 antibody, which comprise: SEQ ID NO:18—rgdslrshyas (CDR1), SEQ ID NO:19—gknnrps (CDR2) and SEQ ID NO:20—ssrdksgsrlsv (CDR3). Finally, the light chain (VLCH1) of the VRC07/PGT128-10E8 right arm (top) comprises the VRC07 Light Chain VL and IgG CH1 sequences, which are SEQ ID NO:27—qygs (CDR1), SEQ ID NO:28—sgst (CDR2), and SEQ ID NO:29 qqyef (CDR3).

In another non-limiting embodiment, the disclosure comprises the trispecific antibody termed PGT121/3BNC117-PGDM1400. As can be seen from FIG. 22, PGT121/3BNC117-PGDM1400 comprises a contiguous polypeptide that is the PGT121 Heavy Chain Knob PGDM1400VH sequence, which comprises these VH CDRs in the N→C orientation: SEQ ID NO:33—GASISDSY (CDR1); SEQ ID NO:34—VHKSGDT (CDR2), and SEQ ID NO:35—TLHGRRIYGIVAFNEWFTYFYMDV (CDR3) from PGT121 VH, followed by VH CDR sequences from the PGDM1400 antibody, and have the PGDM1400 VH CDR sequences SEQ ID NO:30—GNTLKTYD (CDR1), SEQ ID NO:31—ISHEGDKK (CDR2), and SEQ ID NO:32—CAKGSKHRLRDYALYDDDGALNWAVDVDYLSNLEFW (CDR3). This is paired with the PGT121 Light Chain comprising SEQ ID NO:36—SLGSRA (CDR1), SEQ ID NO:37 NNQ (CDR2) and SEQ ID NO:38—HIWDSRVPTKWV (CDR3). The other half of PGT121/3BNC117-PGDM1400 that pairs with the foregoing PGT121 Heavy Chain Knob PGDM1400VH sequence is 3BNC117 Heavy Chain HoleCross PGDM1400VL and comprises from the N→C orientation a contiguous polypeptide that comprises the 3BNC117 VH CDR sequences SEQ ID NO:39—DYFIH (CDR1), SEQ ID NO: 40—WINPKTGQPNNPRQFQG (CDR2) and SEQ ID NO:41—QRSDYWD (CDR3), followed by the PGDM1400 VL sequences SEQ ID NO:42—HSLIHGDRNNY (CDR1), SEQ ID NO: 43—LAS (CDR2) and SEQ ID NO:44—CMQGRESPWTF (CDR3). This is paired with the 3BNC117 Light Chain VLCH1 sequences, which comprises the CDR sequences SEQ ID NO:45—QANGYLN (CDR1), SEQ ID NO:46—DGSKLER (CDR2) and SEQ ID NO:47—QVYEF (CDR3).

The produced fusion antibodies can be evaluated in in vitro assays to assess their functionality, e.g., binding to the HIV envelope and anti-HIV potency and breadth. In specific embodiments, this disclosure provides potent and broad tri-specific fusion antibodies, with potency and breadth being defined as hereinabove. These antibodies are described in more details in the Examples section.

In certain embodiments, the disclosure comprises a tri-specific antibody of this disclosure in a complex with one or more HIV particles, wherein the complex comprises a non-covalent interaction between an HIV antigenic molecule and the tri-specific antibody, i.e., a non-covalent interaction between at least one epitope recognition portion of a tri-specific antibody (VH, and VL segments, i.e., the tri-specific antibody CDR-containing segments, for example) and an epitope present on the HIV particle, such as on the HIV envelope.

Modifications to Antibodies
Humanization and Primatization

In cases where the tri-specific fusion antibody or the three antibodies forming the tri-specific fusion antibody are non-human antibodies, the antibody can be "humanized" to reduce immunogenicity to a human recipient. Methods for humanizing non-human antibodies have been described in the art. See, e.g., Jones et al., Nature 321:522-525 (1986); Riechmann et al, Nature 332:323-327 (1988); Verhoeyen et al., Science 239:1534-1536 (1988), and U.S. Pat. No. 4,816,567. Generally, residues from the variable domain of a non-human antibody are "imported" into a human immunoglobulin molecule, resulting in antibodies in which some hypervariable region residues and possibly some FR residues of a human antibody are substituted by residues from analogous sites of non-human antibodies. It is important to humanize a non-human antibody while retaining high affinity for the antigen. To this end, three dimensional immunoglobulin models are commonly available and suitable for use in analyzing proposed humanized sequences in comparison to the parental non-human antibodies. Such analysis permits identification of residues likely involved in recognition and binding of the antigen, and therefore rational design of humanized sequences that retain the specificity and affinity for the antigen.

In specific embodiments, tri-specific fusion antibodies are formed from anti-HIV human or humanized antibodies.

Similarly, a tri-specific fusion antibody or the three antibodies forming the fusion can be "primatized" to reduce immunogenicity to another primate, non-human recipient, e.g., a rhesus recipient. Residues from the variable domain of a donor antibody (such as a non-primate antibody or an antibody of a primate species different from the recipient primate) are "imported" into a nonhuman primate recipient immunoglobulin molecule, resulting in antibodies in which some hypervariable region residues and possibly some FR residues of a nonhuman primate antibody are substituted by residues from analogous sites of donor antibodies. Alternatively, primatized antibodies can be made for use in a desirable primate species by using a recipient immunoglobulin having non-primate sequences or sequences from a different primate species by introducing the Fc fragment, and/or residues, including particularly framework region residues, from the desirable primate, into the recipient immunoglobulin.

Affinity Maturation

One or more hypervariable region residues of an antibody can be substituted to select for variants that have improved biological properties relative to the parent antibody by employing, e.g., affinity maturation using phage or yeast display. For example, the Fab region of an anti-HIV antibody can be mutated at several sites selected based on available structural information to generate all possible amino substitutions at each site. The antibody variants thus generated are displayed in a monovalent fashion from phage particles or on the surface of yeast cells. The displayed variants are then screened for their biological activity (e.g. binding affinity).

Modifications to the Fc Region

The fusion antibody or the intact antibody used in forming the fusion, which can be of any IgG isotype from any primate species including human, can be modified to improve certain biological properties of the antibody, e.g., to improve stability, to enhance or reduce effector functions such as antigen-dependent cell-mediated cyotoxicity (ADCC) and/or complement dependent cytotoxicity (CDC) of the antibody, improved or decreased internalization and/or recycling, among others.

For example, the Fc fragment of some antibodies (derived from human Ig4) can be replaced with human IgG1 that increases effector function mediated through FcRs (except FcRn). Such modification may improve the stability of the resulting antibody by about 5 fold. In another example, the IgG1 Fc fragment can be modified to improve the recycling of the antibody via the antibody salvage pathway.

Still another type of modification involves alteration of the glycosylation pattern of a parent antibody, including deletions of one or more carbohydrate moieties found in the parent antibody, or addition of one or more carbohydrates (via addition of one or more glycosylation sites) that are not present in the parent antibody Pharmaceutical Formulations Pharmaceutical formulations of the fusion antibody proteins disclosed can be prepared by mixing a fusion protein with optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The formulation can contain more than one active compound, e.g., one or more fusion antibodies, in combination with one or more additional beneficial compound for preventing and treating HIV infections.

The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

Methods of Treatment and Prevention

In a further aspect, the tri-specific fusion antibodies disclosed herein, optionally provided in pharmaceutically acceptable carrier, are employed for the treatment and prevention of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection.

The term "prevention" of HIV infection means the onset of HIV infection is delayed, and/or the incidence or likelihood of HIV infection is reduced or eliminated.

The term "prevention" of HIV transmission means the incidence or likelihood of HIV being transmitted from one individual to another (e.g., from an HIV-positive woman to the child during pregnancy, labor or delivery, or breastfeeding) is reduced or eliminated.

The term "subject" refers to any primate subject, including human and rhesus subjects.

To treat and/or prevent HIV infection, a therapeutic amount of a fusion antibody disclosed herein is administered to a subject in need.

The term "therapeutically effective amount" means the dose required to effect an inhibition of HIV infection so as to treat and/or prevent HIV infection. The dosage of a fusion antibody depends on the disease state and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of a fusion antibody for the administration to adult humans parenterally is in the range of about 0.1 to 20 mg/kg of patient body weight per day, once a week, or even once a month, with the typical initial range used being in the range of about 2 to 10 mg/kg. Since the antibodies will eventually be cleared from the bloodstream, re-administration may be required. Alternatively, implantation or injection of the fusion antibodies provided in a controlled release matrix can be employed.

The fusion antibodies can be administered to the subject by standard routes, including the oral, transdermal, parenteral (e.g., intravenous, intraperitoneal, intradermal, subcutaneous or intramuscular). In addition, the antibodies can be introduced into the body, by injection or by surgical implantation or attachment such that a significant amount of a desirable antibody is able to enter blood stream in a controlled release fashion.

The description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The present description is further illustrated by the following examples, which should not be construed as limiting in any way. The contents of all cited references (including literature references, issued patents, and published patent applications as cited throughout this application) are hereby expressly incorporated by reference.

Example 1

A number of trispecific antibodies targeting different epitopes on the HIV envelope were generated and tested and are listed in Table 1.

Table 1. Tri-specific fusion antibodies and their HIV epitope targets.

TABLE 1

Tri-specific fusion antibodies and their HIV epitope targets.

| Trispecific Antibodies | HIV Epitope Target |
| --- | --- |
| VRC07/PGT128-10E8 | CD4bs, V3, gp41 |
| VRC07/10E8-PGT128 | CD4bs, gp41, V3 |
| VRC07/PGT128-PGT151 | CD4bs, V3, gp120/41 |
| VRC07/PGT151-PGT128 | CD4bs, gp120/41, V3 |
| VRC07/PGT128-PGT145 | CD4bs, V3, V1/V2 |
| VRC07/PGT128-PGDM1400 | CD4bs, V3, V1/V2 |
| 3BNC117/PGT145-PGT128 | CD4bs, V1/V2, V3 |
| 3BNC117/PGT145-10E8 | CD4bs, V1/V2, gp41 |
| 3BNC117/10E8-PGT128 | CD4bs, gp41, V3 |
| PGT128/PGT151-VRC07 | V3, gp120/41, CD4bs |
| PGT145/10E8-PGT128 | V1/V2, gp41, V3 |
| PGDM1400/PGT121-PGT151 | V1/V2, V3, gp120/41 |
| VRC07/PGT121-PGT151 | CD4bs, V3, gp120/41 |
| VRC07PGT151-PGDM1400 | CD4bs, gp120/41, V1/V2 |
| PGT121/PGT151-PGDM1400 | V3, gp120/41, V1/V2 |
| VRC07/PGT121-PGDM1400 | CD4bs, V3, V1/V2 |
| PGT121/PGDM1400-PGT151 | V3, V1/V2, gp120/41 |
| PGT121/3BNC117-PGT151 | V3, CD4bs, gp120/41 |
| PGT128/3BNC117-PDGM1400 | V3, CD4bs, V1/V2 |
| 10-1074/3BNC117-PGDM1400 | V3, CD4bs, V1/V2 |

Example 2. Tri-Specific Fusion Antibody: VRC07/PGT128-10E8 Activity

A tri-specific fusion antibody was generated, containing the PGT128, VRC07 and 10E8 antibody domains, which target the V3, CD4 binding site and gp41 domains, respectively, on the HIV envelope. See FIG. 2. The graphs indicate the HIV neutralization activity of the trispecific antibody (07/128-10E8) against a number of different HIV-envelope pseudotyped viruses. For comparison, the neutralization activities of two of the parental mAbs used to derive this trispecific antibody were tested alone and in combination (VRC07, PGT128 and 07+128), and a bispecific antibody comprised of these two parental antibodies (VRC07/128) also was tested.

Example 3. Tri-Specific Fusion Antibody: VRC07, PGT128 and PCT151 Combination

Two versions of tri-specific antibodies were generated that contained the PGT128, VRC07 and PGT151 antibody domains, which target the V3, CD4 binding site and gp120/41 domains, respectively, on the HIV envelope. In one variation, the C-terminal domain of the trispecific antibody contained the PGT151 antibody moiety and, in a second variation, the C-terminal domain of the trispecific antibody contained the PGT128 antibody. The graphs indicate the HIV neutralization activity of the trispecific antibodies (128/07-151 and 151/07-128) against a number of different HIV-envelope pseudotyped viruses. For comparison, the neutralization activities of the three parental mAbs used to derive this trispecific antibody were tested alone and in combination (VRC07, PGT128, PGT151, 128+07+151), and a bispecific antibody comprised of two of the parental antibodies (128/07 (XM)) was also tested (see FIG. 3).

Example 4. Tri-Specific Fusion Antibody: VRC07, PGT128 and PGT151 Combination

Figure 4:
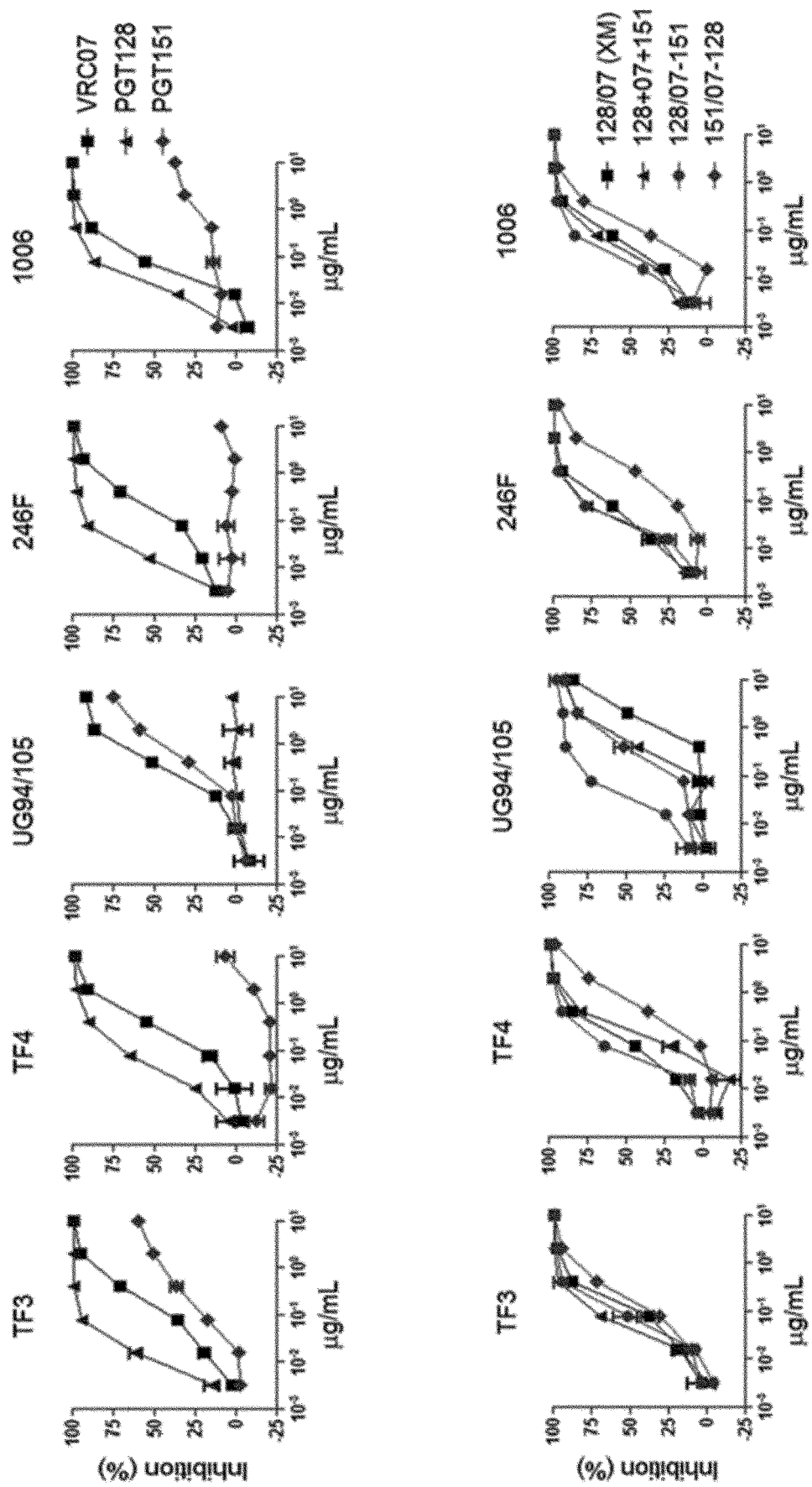
FIG. 4 shows the different HIV neutralization activities of tri-specific molecules containing the antibody domains PGT128, VRC07 and PGT151 where, in one variation, the PGT151 domain is placed at the C-terminus of the trispecific molecule and, in another variation, the PGT128 domain is placed at the C-terminus of the trispecific molecule.

Even though two different tri-specific antibodies contain the same three antibody domains, the orientation and placement of these antibody domains along the molecule affect the neutralization activity of the tri-specific antibody. FIG. 4 demonstrates the different HIV neutralization activities of tri-specific molecules containing the antibody domains PGT128, VRC07 and PGT151 where, in one variation, the PGT151 domain is placed at the C-terminus of the trispecific molecule and, in another variation, the PGT128 domain is placed at the C-terminus of the trispecific molecule. Orientation of the three antibody domains matters: PGT128/VRC07-PGT151 is more active than PGT151/VRC07-PGT128.

Example 5. Tri-Specific Fusion Antibody: VRC07, PGT128 and PGT145 Combination

Figure 5:
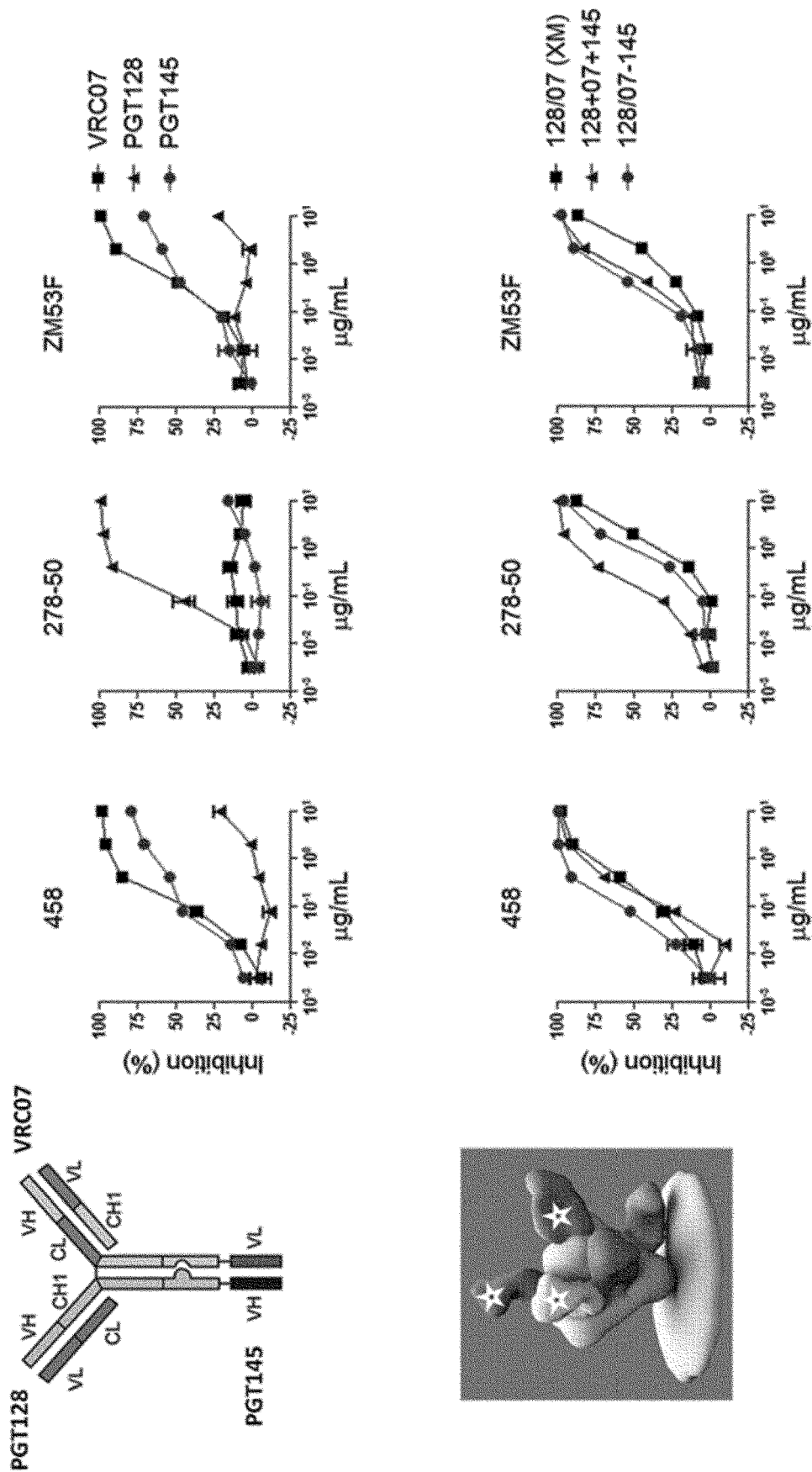
FIG. 5 shows a tri-specific antibody containing the PGT128, VRC07 and PGT145 antibody domains, which target the V3, CD4 binding site and V1/V2 domains, respectively, on the HIV envelope, and their activity.
Figure 6:
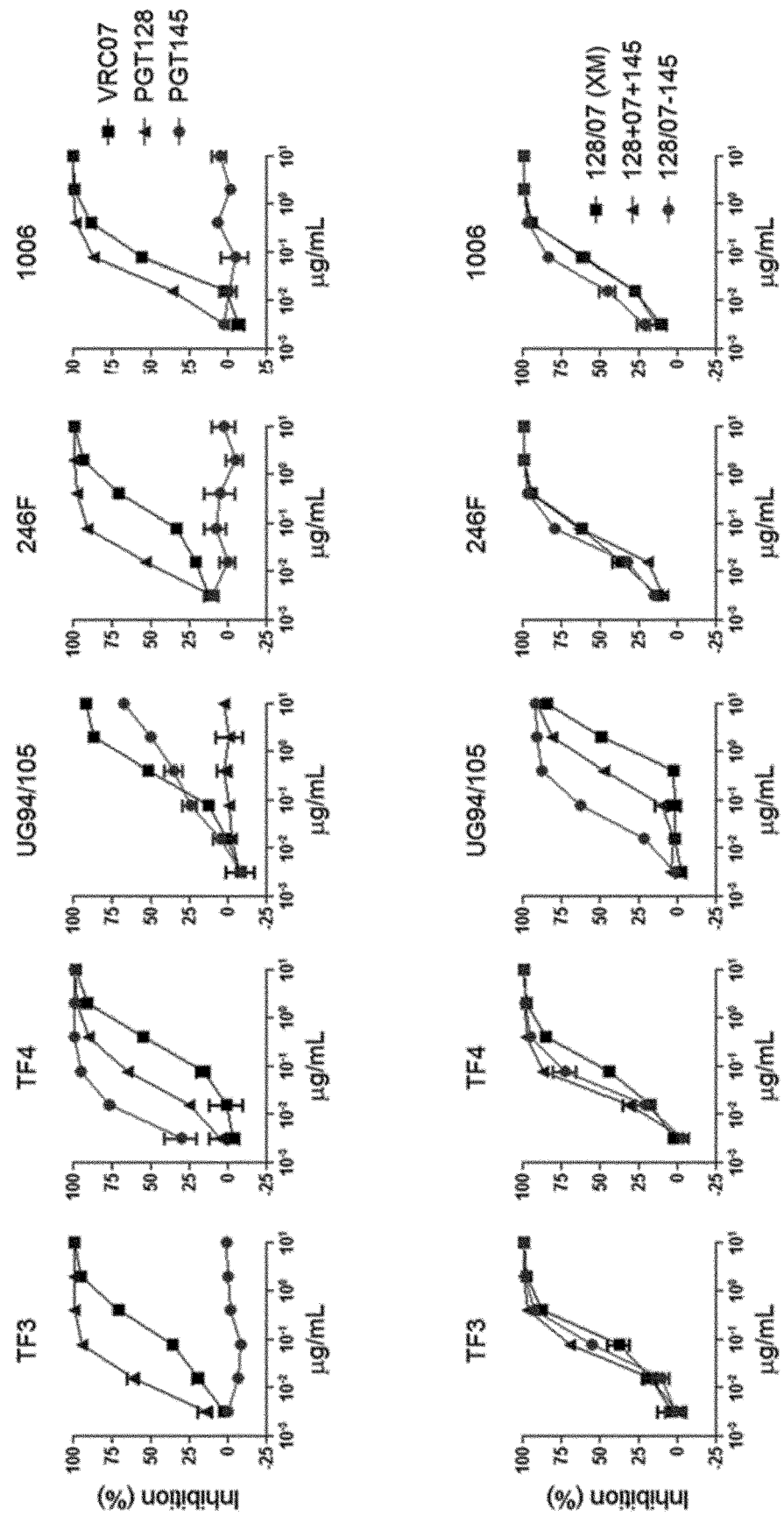
FIG. 6 shows the neutralization activity of the PGT128, VRC07 and PGT145 trispecific antibody against additional HIV-envelope pseudotyped viruses.

A tri-specific antibody, the PGT128, VRC07 and PGT145 antibody domains, which target the V3, CD4 binding site and V1/V2 domains, respectively, on the HIV envelope, was generated (See FIG. 5). The graphs show the HIV neutralization activity of the trispecific antibody (128/07-145) against a number of different HIV-envelope pseudotyped viruses. For comparison, the neutralization activities of the three parental mAbs used to derive this trispecific antibody were tested alone and in combination (VRC07, PGT128, PGT145 and 128+07+145), and a bispecific antibody comprised of two of the parental antibodies (128/07 (XM)) was also tested.

Example 6. Tri-Specific Fusion Antibody: VRC07, PGT128 and PGT145 Combination Activity Against HIV-Envelope Pseudotyped Viruses The neutralization activity of the PGT128, VRC07 and PGT145 trispecific antibody and respective controls of Example 5 also were tested against additional HIV-envelope pseudotyped viruses (see FIG. 6).

Example 7. SEC Analysis of Tri-Specific Antibodies

The biophysical properties of trispecific antibodies were assessed by size exclusion chromatography (SEC). The sharp, single peaks exhibited by each of the trispecific antibodies indicate that these trispecific antibodies display similar monomer and aggregation profiles to traditional monoclonal antibodies (see FIG. 7).

Example 8. Tri-Specific Fusion Antibody vs TriMix Neutralizing Activity In Vitro The neutralization activity of one trispecific antibody, VRC07/PGT128-PGT151 (TriSpe1), was tested for its potency and breadth against a large panel of HIV envelope-pseudotyped viruses representing envelope diversity by geography and clade (see FIG. 8). As a control, the three parental monoclonal antibodies of the trispecific antibody, VRC07, PGT128 and PGT 151 (TriMix1) were mixed together and tested for their combined neutralization activity against the same panel of viruses. The inhibitory concentration 50% (IC50) of TriMix1 was slightly better than that of TriSpe1, and the inhibitory concentration 80% (IC80) and maximum percent inhibition (MPI) were comparable between TriSpe1 and TriMix1.

Example 9. Antiviral Coverage of Tri-Specific Antibody vs. Tri-Mixture (Against 118 Viruses)

Figure 9:
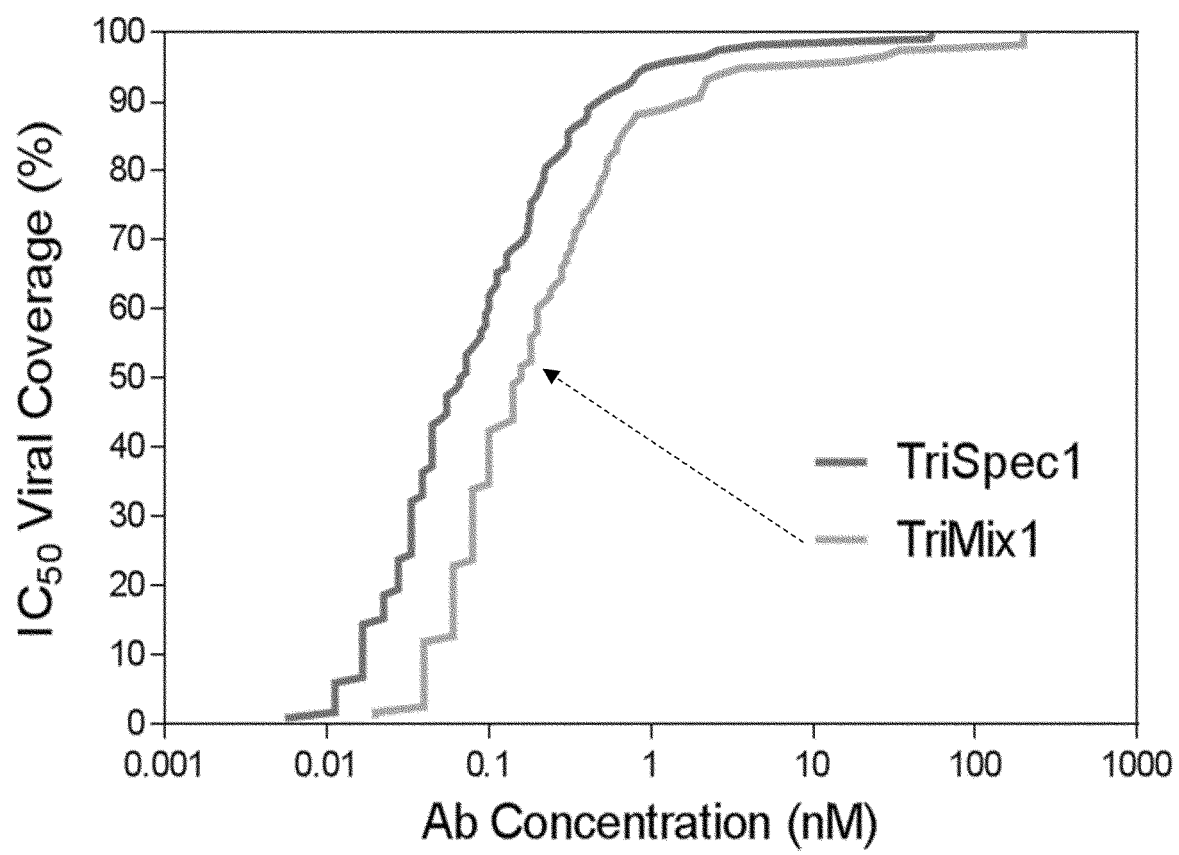
FIG. 9 shows the neutralization activity of one trispecific antibody, VRC07/PGT128-PGT151 (TriSpec1) and a mixture of the three parental monoclonal antibodies of the trispecific antibody, VRC07, PGT128 and PGT 151 (TriMix1) against the same panel of 118 multi-clade viruses and normalized by their molar quantity tested.

The neutralization activity of one trispecific antibody, VRC07/PGT128-PGT151 (TriSpec1) and a mixture of the three parental monoclonal antibodies of the trispecific antibody, VRC07, PGT128 and PGT 151 (TriMix1) against the same panel of pseduotyped viruses and normalized by their molar quantity were tested (see FIG. 9). These data demonstrate that a lower molar quantity of TriSpec1 can achieve the same level of viral inhibitory concentration 50% (IC50) coverage as TriMix1.

Example 10. TriSpec1 Ab IC80 and MPI Analysis

Figure 10:
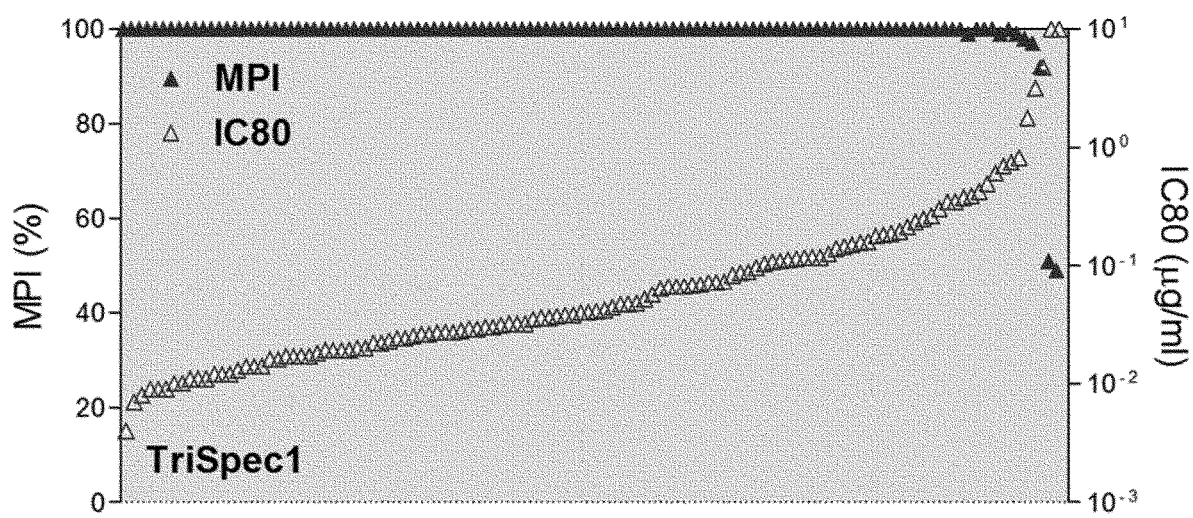
FIG. 10 shows TriSpec1 Ab IC80 and MPI analysis.

TriSpec1 also neutralizes almost every virus in the 118 pseudotyped virus panel as indicated by the maximum percent inhibition (MPI) of TriSpec1 against each virus in the panel (see FIG. 10). The corresponding inhibitory concentration 80% (IC80) of TriSpec1 against each virus in the panel is also presented, and indicates a mean IC80 of 0.0592 ug/mL across the entire virus panel.

Example 11. Mechanism of Action (MOA) Analysis

Figure 11:
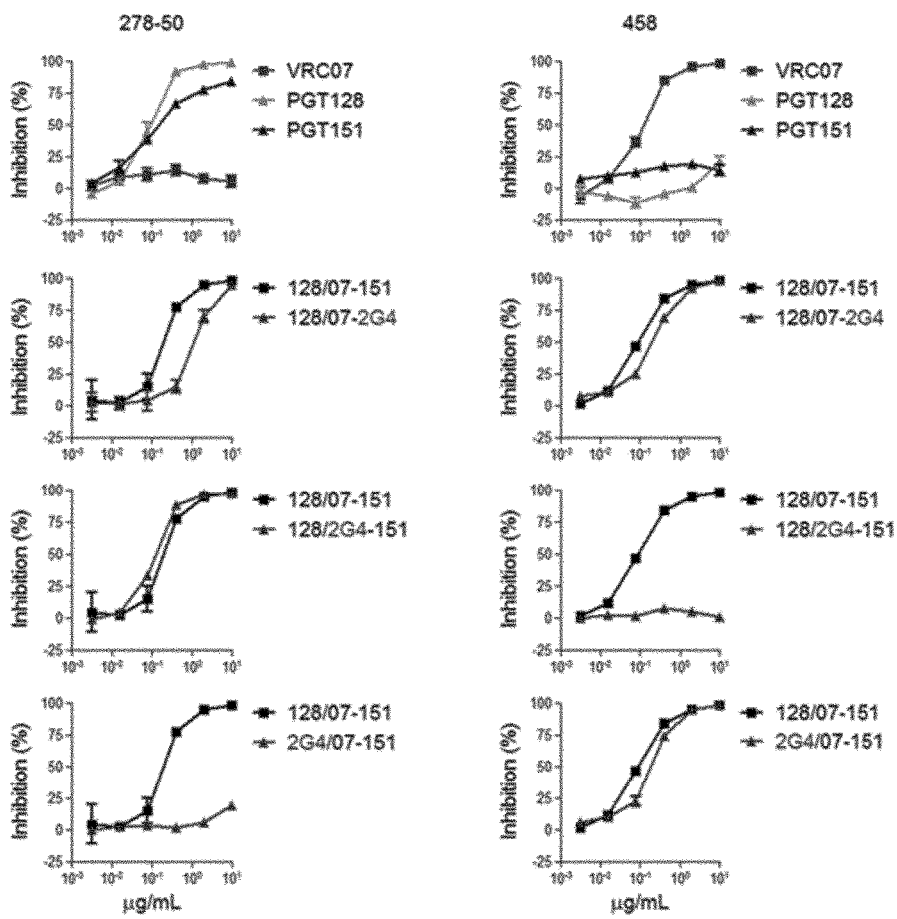
FIG. 11 provides data obtained from analyzing the Mechanism of Action (MOA) of the trispecific antibody 128/07-151.

Additional analysis of the MOA of the trispecific antibodies shown in FIG. 11 were performed. The analysis was initiated with 128/07-151 and systematically knocked out one of the HIV epitope targeting antibody moeities by replacing it with a nonspecific antibody referred to as 2G4. The activity of the trispecific mutants against two different HIV envelope pseudotyped viruses (278-50 and 458) was then tested in vitro. In this way, the relative contribution of each of the three antibody moieties that comprise this trispecific was determined. From this approach it can be concluded that each arm of the trispecific contributes to the overall trispecific's HIV neutralization activity.

Example 12

Figure 12:
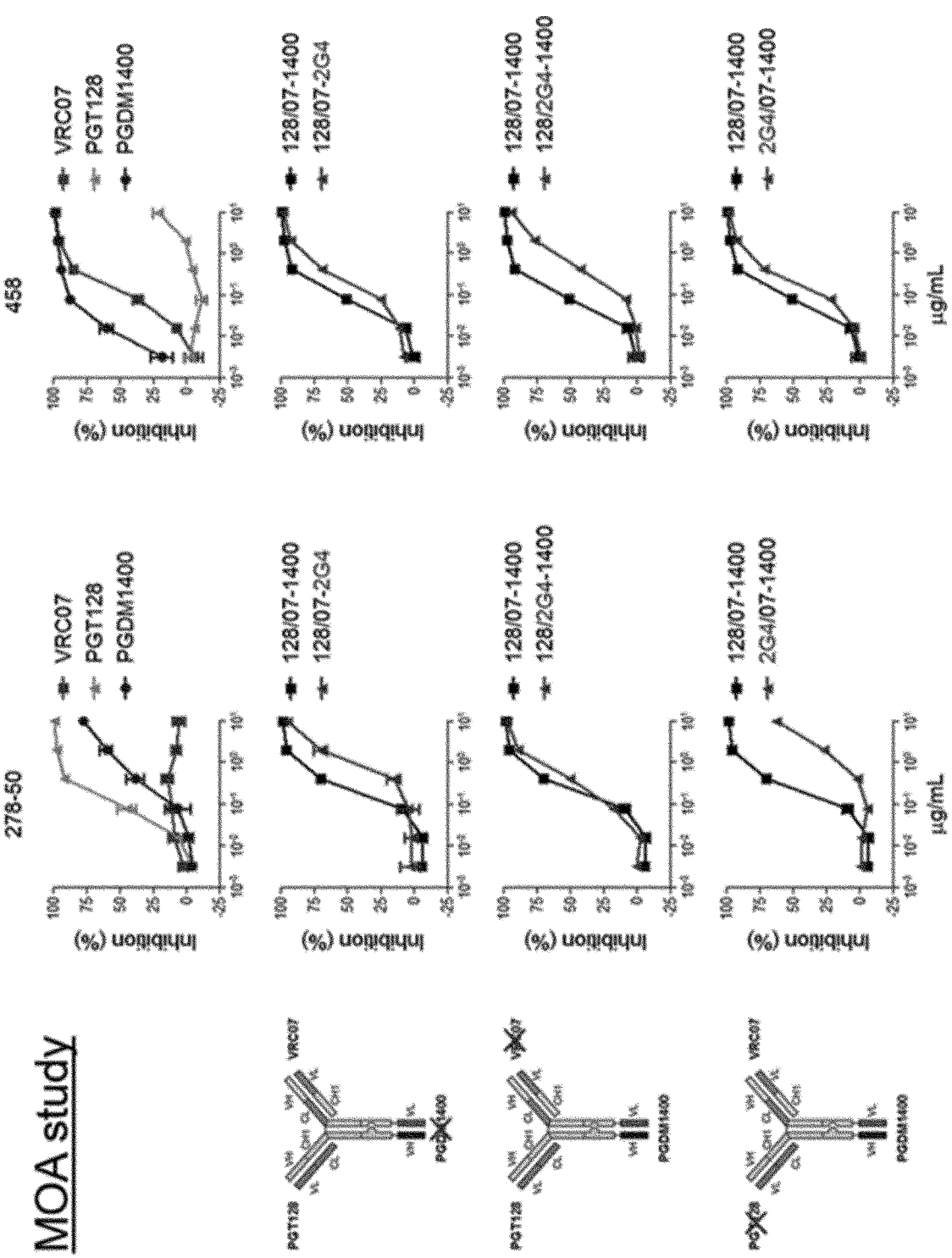
FIG. 12 provides a summary of data obtained from analyzing MOA for trispecific antibody 128/07-1400.

In a similar approach to that taken FIG. 11, a knockout experiment was performed with a second trispecific antibody (128/07-1400) and led to the same determination, i.e. that each arm of the trispecific contributes to the overall trispecific's HIV neutralization activity, as demonstrated by the data shown in FIG. 12.

Example 13

Figure 13:
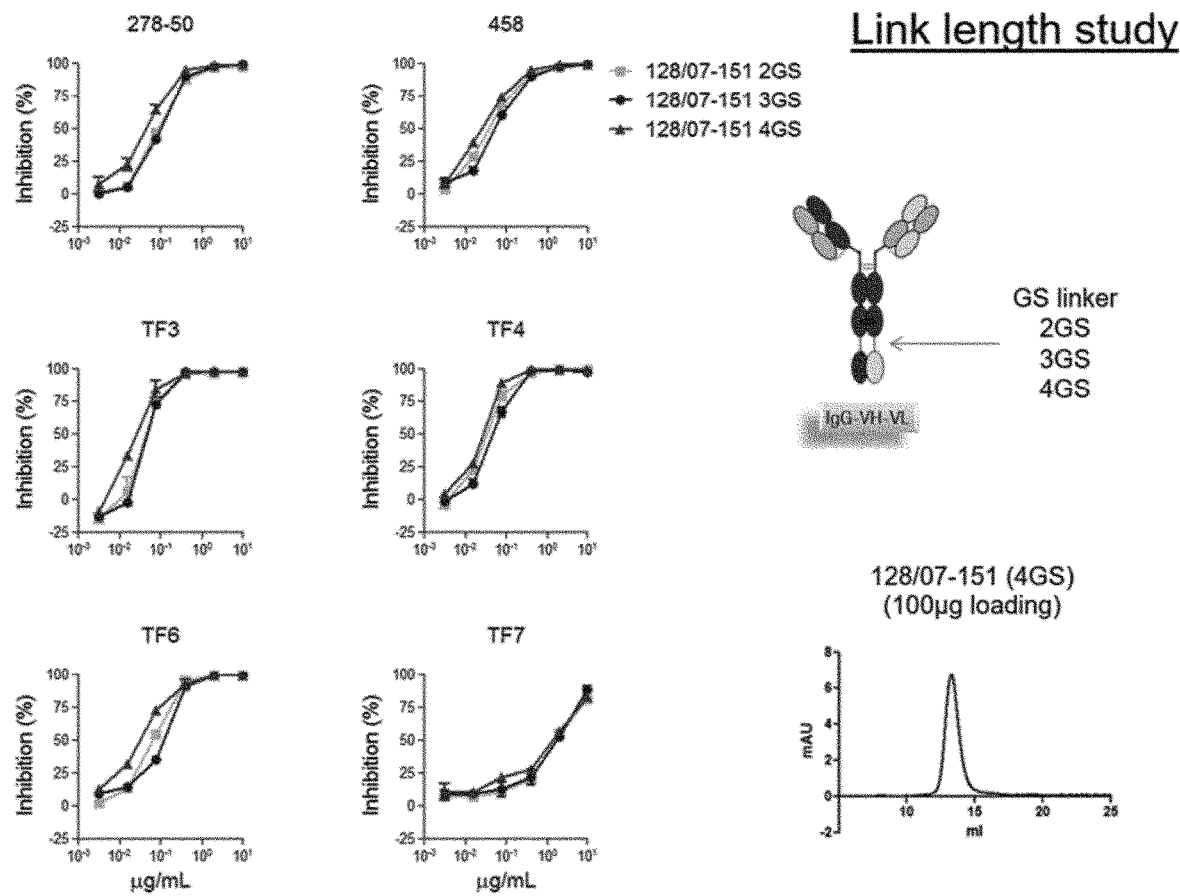
FIG. 13 depicts data obtained by analyzing the effect of including a 2× GS or 4× GS as alternatives to a 3× GS linker.

As described above, certain trispecific constructs of this disclosure comprise a 3× GS linker in order to fuse the C-terminal antibody moiety to the rest of the molecule. FIG. 13 depicts data obtained by analyzing the effect of including a 2× GS or 4× GS as alternatives to the 3× GS linker. In particular, using trispecific 128/07-151, we tested 2× GS, 3× GS, and 4× GS linker length variants and the activity of these different trispecific variants in connection with neutralizing two different HIV strains (278-50 and 458). The results indicate that fusing the C-terminal antibody moiety with a 4× GS linker provided the highest HIV neutralization activity. 128/07-151 with a 4× GS linker also displayed suitable physicochemical homogeneity and minimal aggregation when evaluated by size exclusion chromatography (bottom right graph), which is similar to the size exclusion chromatography data for trispecifics discussed above.

Example 14

Figure 14:
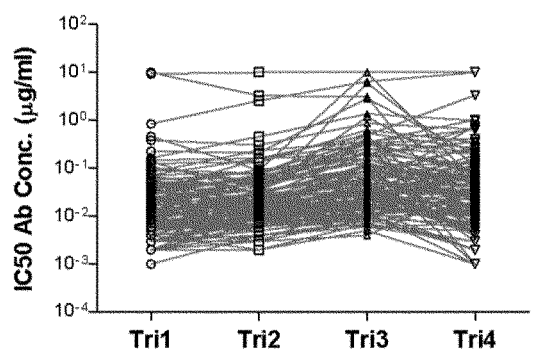
FIG. 14 provides a summary of data obtained from an analysis of the neutralization activity of four distinct different trispecific antibodies.
Figure 14:
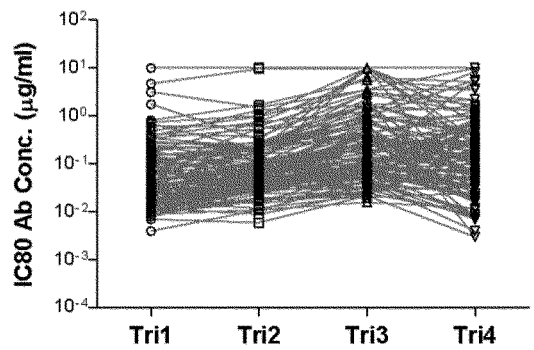
Figure 14:
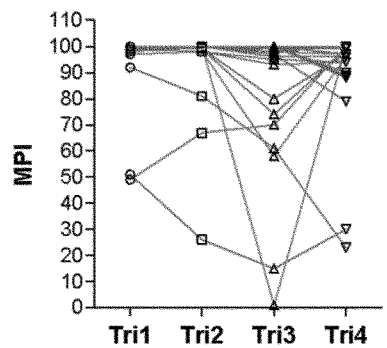

FIG. 14 provides a summary of data obtained from an analysis of the neutralization activity of 4 different trispecific antibodies (with either a 3× GS linker or a 4× GS linker fused to the C-terminal moiety) against a large panel of 118 HIV enveloped pseudotyped viruses. All 4 constructs performed well in this assay, thus indicating favorable potency and breadth against HIV.

Example 15

Figure 15:
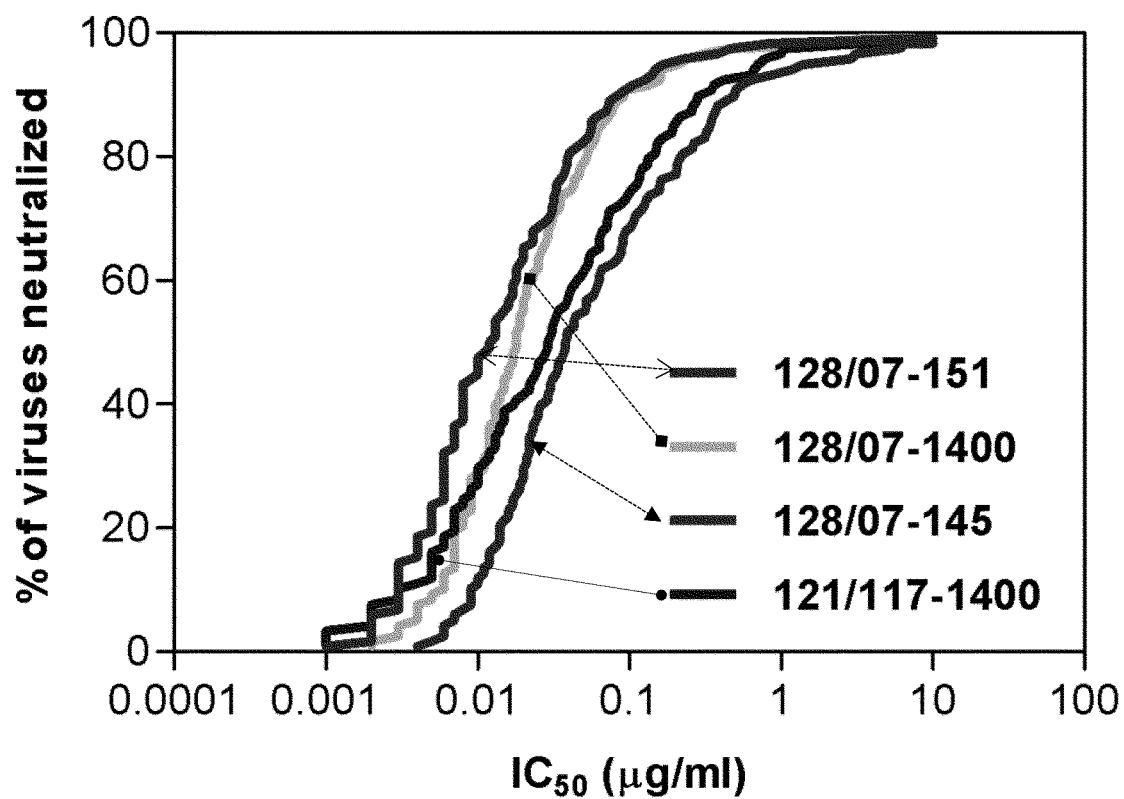
FIG. 15 provides a summary of data obtained by plotting the same data used to generate FIG. 14.

Data summarized in FIG. 15 were obtained by plotting the same data used to generate FIG. 14, and graphically illustrate that all four trispecific antibodies tested neutralize up to or nearly 100% of the 118 pseudovirus panel tested with favorable potency.

Example 16

FIG. 16 provides a tabular summary of data presented in FIGS. 14 and 15 as a calculation of the potency and breadth of the same four trispecific antibodies. The data demonstrate a median 80% inhibitory concentration ($IC_{80}$) ranging from 0.041 ug/mL to 0.172 ug/mL and, at these concentrations, could neutralize between 95.0 and 98.3% of the 118 pseudovirus panel.

Example 17

Figure 17:
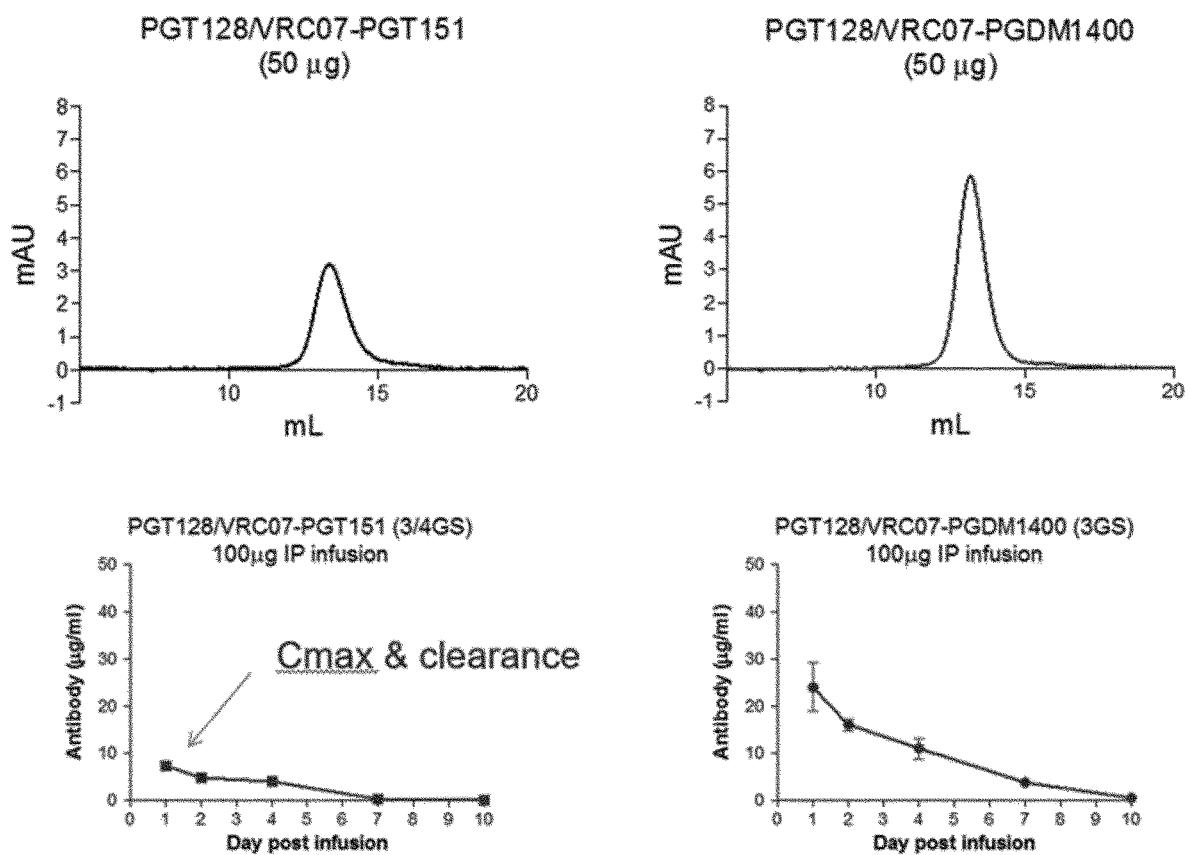
FIG. 17 shows size-exclusion chromatography (SEC) and a summary of pharmacokinetic (PK) data for trispecifics 128/07-151 and 128/07-1400 (3× GS).

Size-exclusion chromatography (SEC) and pharmacokinetics (PK) are provided in FIG. 17 for trispecifics 128/07-151 and 128/07-1400. SEC is shown in the top panels, while data summarized in the bottom panels represent in vivo PK profiles after administration to wild-type mice. Data summarized in the bottom panels demonstrate that 128/07-1400 has distinctly superior in vivo bioavailability and PK profile relative to that of 128/07-151.

Example 18

Figure 18:
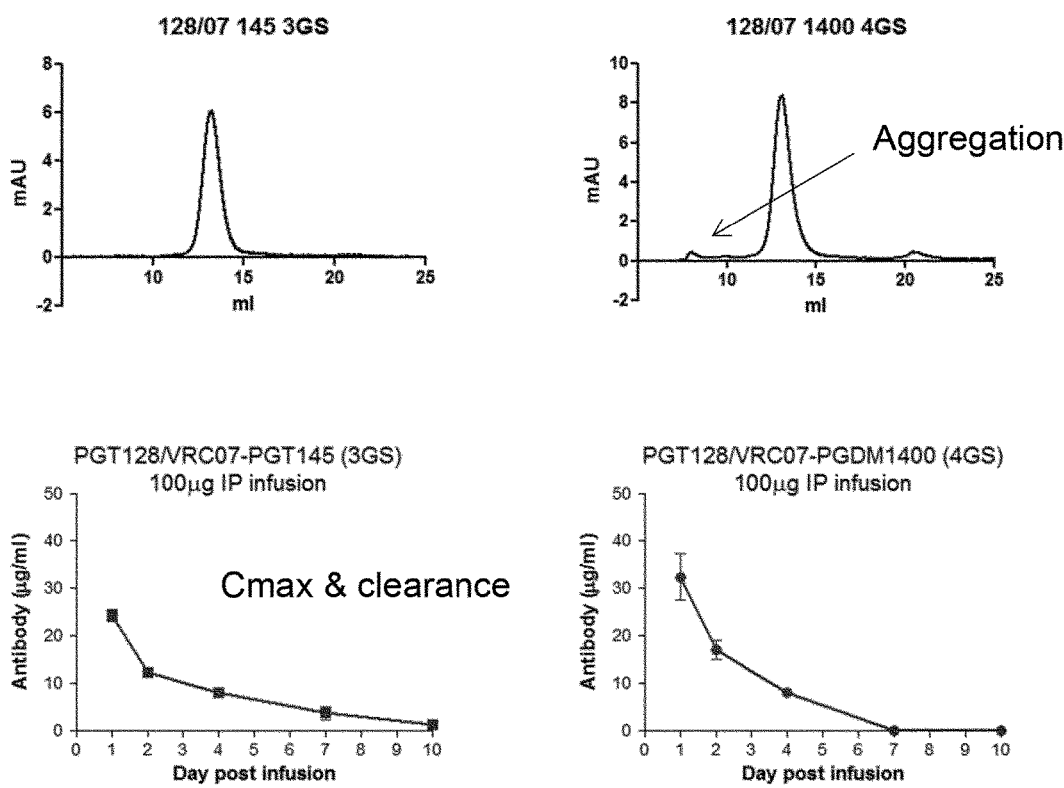
FIG. 18 provides graphical depictions of data obtained from SEC analysis (top panel) and PK profiles (bottom panel).

FIG. 18 provides graphical depictions of data obtained from SEC analysis (top panel) and PK profiles (bottom panel). The SEC data represent the stability, physicochemical homogeneity, and monomeric quality of trispecifics 128/07-145 (3GS) and 128/07-1400 (4GS). 128/07-145 (3GS) has suitable biophysical characteristics, as does 128/07-1400 (4GS) (which also had a minor fraction of aggregation). The bottom panels show in vivo PK profiles after administration to wild-type mice. 128/07-145 (3G) had suitable bioavailability and overall pharmacokinetics; 128/07-1400 (4GS) had improved bioavailability relative to 3GS; 4GS may clear from animals at a faster rate relative to 3G.

Example 19

Figure 19:
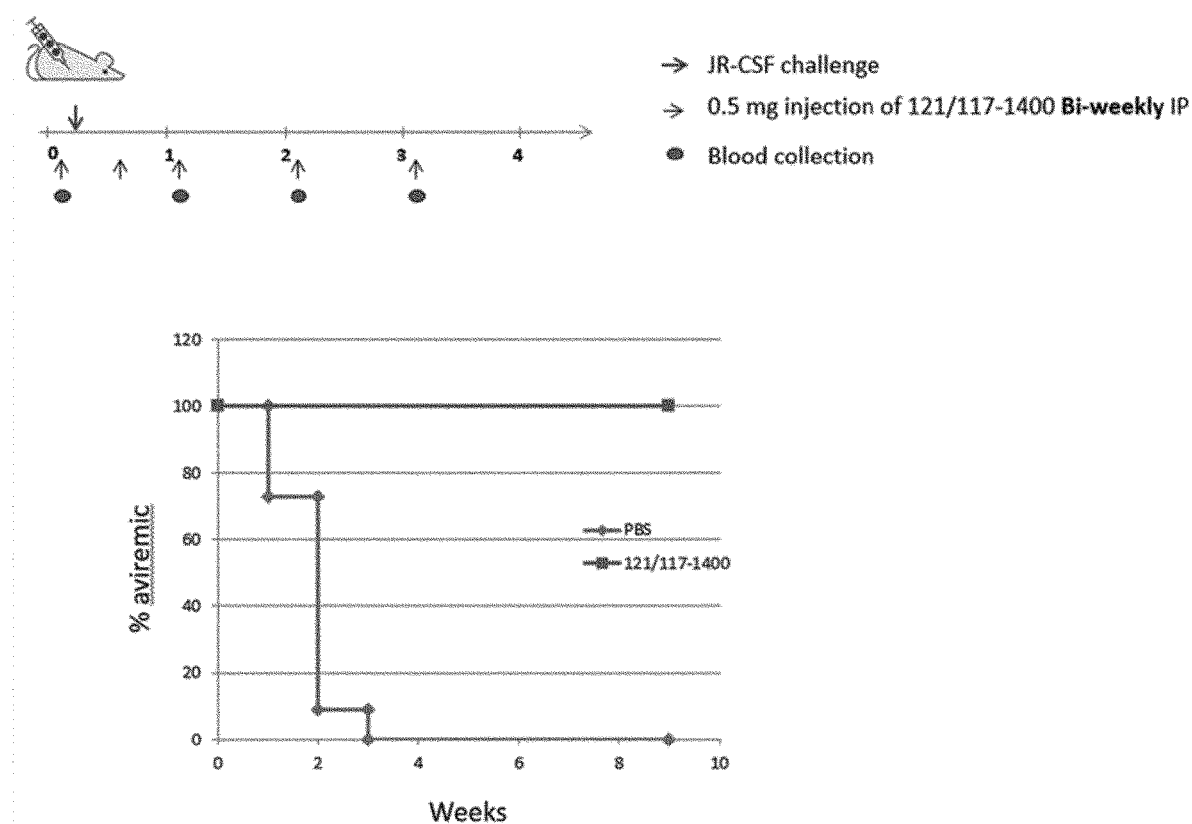
FIG. 19 provides results obtained from an in vivo analysis performed with trispecific 121/117-1400.

An in vivo efficacy analysis with was performed with trispecific 121/117-1400 and data resulting from it are summarized in FIG. 19. To obtain these data, humanized mice received repeated injections with the trispecific antibody, and then were challenged with human $HIV_{JR-CSF}$ while the antibody was present in vivo. While all the control animals that did not receive antibody became infected with HIV-1 after viral challenge (blue line/diamonds), 100% of those animals that received the trispecific antibody remained protected and HIV negative (red line/squares).

Example 20

As shown in FIG. 20, an additional trispecific antibody relative to those discussed above, comprised of the PGT121, 3BNC117 and PGT151 antibody moieties in a single molecule, neutralizes two different transmitted-founder pseudotyped viruses (TF4 and TF6) just as well as a combination of the 3 mAb mixtures of PGT121, 3BNC117 and PGT151.

Example 21

As shown in FIG. 21, two additional trispecific antibodies relative to those discussed above, comprising 1) the PGT128, 3BNC117 and PDGM1400 antibody moieties in a single molecule, and 2) the 10-1074, 3BNC117, PGDM1400 antibody moieties in a single molecule, neutralize two different pseudotyped viruses (1006 and 246F) with efficacy similar to another trispecific antibody discussed above, PGT128/VRC07-PGDM1400.

What is claimed is:

1. A tri-specific antibody, comprising first, second and third antigen-binding sites which are capable of binding with specificity to first, second and third distinct epitopes that are comprised by a Human Immunodeficiency Virus (HIV), wherein the first, second and third antigen-binding sites comprise antigen binding sites of PGT128/3BNC117-PGDM1400 antibodies, and wherein the antigen binding site of the PGDM1400 antibody is at the C-terminus of the tri-specific antibody, and wherein the antigen binding site of the PGDM1400 antibody is optionally linked to the C-terminus of the heavy chain of the tri-specific antibody by a GS linker.

2. The tri-specific antibody of claim 1, wherein said anti-HIV antibody is humanized.

3. A method of treating a subject infected with Human Immunodeficiency Virus (HIV) comprising administering to the subject a therapeutically effective amount of a tri-specific antibody of claim 1.

4. A method of inhibiting Human Immunodeficiency Virus (HIV)-positive pregnant subject from transmitting the HIV to the fetus or newborn, comprising administering to the subject and/or the newborn a therapeutically effective amount of the tri-specific antibody according to claim 1.

5. A pharmaceutical composition comprising a tri-specific antibody of claim 1.

6. The method of claim 3, wherein said anti-HIV antibody is humanized.

7. The pharmaceutical composition of claim 5, wherein anti-HIV antibody is humanized.

8. The method of claim 4, wherein anti-HIV antibody is humanized.

* * * * *

SEQUENCE LISTING

```
<160> NUMBER OF SEQ ID NOS: 54

<210> SEQ ID NO 1
<211> LENGTH: 8
<212> TYPE: PRT
<213> ORGANISM: Human

<400> SEQUENCE: 1

Asn Ser Phe Trp Gly Trp Val Arg
1               5

<210> SEQ ID NO 2
<211> LENGTH: 8
<212> TYPE: PRT
<213> ORGANISM: human

<400> SEQUENCE: 2

Ser Tyr Trp Asn Arg Gly Trp Thr
1               5

<210> SEQ ID NO 3
<211> LENGTH: 19
<212> TYPE: PRT
<213> ORGANISM: human

<400> SEQUENCE: 3

Phe Gly Gly Glu Val Leu Arg Tyr Thr Asp Trp Pro Lys Pro Ala Trp
1               5                   10                  15

Val Asp Leu

<210> SEQ ID NO 4
<211> LENGTH: 8
<212> TYPE: PRT
<213> ORGANISM: human

<400> SEQUENCE: 4

Gly Asn Ser Phe Ser Asn His Asp
```

```
1               5
```

```
<210> SEQ ID NO 5
<211> LENGTH: 8
<212> TYPE: PRT
<213> ORGANISM: human

<400> SEQUENCE: 5

Met Ser His Glu Gly Asp Lys Thr
1               5

<210> SEQ ID NO 6
<211> LENGTH: 31
<212> TYPE: PRT
<213> ORGANISM: human

<400> SEQUENCE: 6

Gly Ser Lys His Arg Leu Arg Asp Tyr Phe Leu Tyr Asn Glu Tyr Gly
1               5                   10                  15

Pro Asn Tyr Glu Glu Trp Gly Asp Tyr Leu Ala Thr Leu Asp Val
            20                  25                  30

<210> SEQ ID NO 7
<211> LENGTH: 6
<212> TYPE: PRT
<213> ORGANISM: human

<400> SEQUENCE: 7

Gly Thr Ser Asn Asn Phe
1               5

<210> SEQ ID NO 8
<211> LENGTH: 3
<212> TYPE: PRT
<213> ORGANISM: human

<400> SEQUENCE: 8

Asp Val Asn
1

<210> SEQ ID NO 9
<211> LENGTH: 5
<212> TYPE: PRT
<213> ORGANISM: human

<400> SEQUENCE: 9

Asn Cys Pro Ile Asn
1               5

<210> SEQ ID NO 10
<211> LENGTH: 17
<212> TYPE: PRT
<213> ORGANISM: human

<400> SEQUENCE: 10

Trp Met Lys Pro Arg Gly Gly Ala Val Ser Tyr Ala Arg Gln Leu Gln
1               5                   10                  15

Gly

<210> SEQ ID NO 11
<211> LENGTH: 16
<212> TYPE: PRT
<213> ORGANISM: human
```

-continued

```
<400> SEQUENCE: 11

Gly Lys Tyr Cys Thr Ala Arg Asp Tyr Tyr Asn Trp Asp Phe Glu His
1               5                   10                  15

<210> SEQ ID NO 12
<211> LENGTH: 11
<212> TYPE: PRT
<213> ORGANISM: human

<400> SEQUENCE: 12

His Ser Leu Gln His Ser Thr Gly Ala Asn Tyr
1               5                   10

<210> SEQ ID NO 13
<211> LENGTH: 3
<212> TYPE: PRT
<213> ORGANISM: human

<400> SEQUENCE: 13

Leu Ala Thr
1

<210> SEQ ID NO 14
<211> LENGTH: 9
<212> TYPE: PRT
<213> ORGANISM: human

<400> SEQUENCE: 14

Met Gln Gly Leu His Ser Pro Trp Thr
1               5

<210> SEQ ID NO 15
<211> LENGTH: 8
<212> TYPE: PRT
<213> ORGANISM: human

<400> SEQUENCE: 15

Gly Phe Asp Phe Asp Asn Ala Trp
1               5

<210> SEQ ID NO 16
<211> LENGTH: 10
<212> TYPE: PRT
<213> ORGANISM: human

<400> SEQUENCE: 16

Ile Thr Gly Pro Gly Glu Gly Trp Ser Val
1               5                   10

<210> SEQ ID NO 17
<211> LENGTH: 20
<212> TYPE: PRT
<213> ORGANISM: human

<400> SEQUENCE: 17

Thr Gly Lys Tyr Tyr Asp Phe Trp Ser Gly Tyr Pro Pro Gly Glu Glu
1               5                   10                  15

Tyr Phe Gln Asp
            20

<210> SEQ ID NO 18
<211> LENGTH: 11
<212> TYPE: PRT
<213> ORGANISM: human
```

-continued

<400> SEQUENCE: 18

Arg Gly Asp Ser Leu Arg Ser His Tyr Ala Ser
1               5                   10

<210> SEQ ID NO 19
<211> LENGTH: 7
<212> TYPE: PRT
<213> ORGANISM: human

<400> SEQUENCE: 19

Gly Lys Asn Asn Arg Pro Ser
1               5

<210> SEQ ID NO 20
<211> LENGTH: 12
<212> TYPE: PRT
<213> ORGANISM: human

<400> SEQUENCE: 20

Ser Ser Arg Asp Lys Ser Gly Ser Arg Leu Ser Val
1               5                   10

<210> SEQ ID NO 21
<211> LENGTH: 8
<212> TYPE: PRT
<213> ORGANISM: human

<400> SEQUENCE: 21

Asp Phe Pro Phe Ser Lys Tyr Pro
1               5

<210> SEQ ID NO 22
<211> LENGTH: 8
<212> TYPE: PRT
<213> ORGANISM: human

<400> SEQUENCE: 22

Ile Ser Gly Asp Ala Trp His Val
1               5

<210> SEQ ID NO 23
<211> LENGTH: 28
<212> TYPE: PRT
<213> ORGANISM: human

<400> SEQUENCE: 23

Ala Arg Met Phe Gln Glu Ser Gly Pro Pro Arg Leu Asp Arg Trp Ser
1               5                   10                  15

Gly Arg Asn Tyr Tyr Tyr Tyr Ser Gly Met Asp Val
            20                  25

<210> SEQ ID NO 24
<211> LENGTH: 11
<212> TYPE: PRT
<213> ORGANISM: human

<400> SEQUENCE: 24

Glu Ser Leu Arg Gln Ser Asn Gly Lys Thr Ser
1               5                   10

<210> SEQ ID NO 25
<211> LENGTH: 3
<212> TYPE: PRT

```
<213> ORGANISM: human

<400> SEQUENCE: 25

Glu Val Ser
1

<210> SEQ ID NO 26
<211> LENGTH: 9
<212> TYPE: PRT
<213> ORGANISM: human

<400> SEQUENCE: 26

Met Gln Ser Lys Asp Phe Pro Leu Thr
1               5

<210> SEQ ID NO 27
<211> LENGTH: 4
<212> TYPE: PRT
<213> ORGANISM: human

<400> SEQUENCE: 27

Gln Tyr Gly Ser
1

<210> SEQ ID NO 28
<211> LENGTH: 4
<212> TYPE: PRT
<213> ORGANISM: human

<400> SEQUENCE: 28

Ser Gly Ser Thr
1

<210> SEQ ID NO 29
<211> LENGTH: 5
<212> TYPE: PRT
<213> ORGANISM: human

<400> SEQUENCE: 29

Gln Gln Tyr Glu Phe
1               5

<210> SEQ ID NO 30
<211> LENGTH: 8
<212> TYPE: PRT
<213> ORGANISM: human

<400> SEQUENCE: 30

Gly Asn Thr Leu Lys Thr Tyr Asp
1               5

<210> SEQ ID NO 31
<211> LENGTH: 8
<212> TYPE: PRT
<213> ORGANISM: human

<400> SEQUENCE: 31

Ile Ser His Glu Gly Asp Lys Lys
1               5

<210> SEQ ID NO 32
<211> LENGTH: 36
<212> TYPE: PRT
<213> ORGANISM: human
```

-continued

<400> SEQUENCE: 32

Cys Ala Lys Gly Ser Lys His Arg Leu Arg Asp Tyr Ala Leu Tyr Asp
1               5                   10                  15

Asp Asp Gly Ala Leu Asn Trp Ala Val Asp Val Asp Tyr Leu Ser Asn
            20                  25                  30

Leu Glu Phe Trp
        35

<210> SEQ ID NO 33
<211> LENGTH: 8
<212> TYPE: PRT
<213> ORGANISM: human

<400> SEQUENCE: 33

Gly Ala Ser Ile Ser Asp Ser Tyr
1               5

<210> SEQ ID NO 34
<211> LENGTH: 7
<212> TYPE: PRT
<213> ORGANISM: human

<400> SEQUENCE: 34

Val His Lys Ser Gly Asp Thr
1               5

<210> SEQ ID NO 35
<211> LENGTH: 24
<212> TYPE: PRT
<213> ORGANISM: human

<400> SEQUENCE: 35

Thr Leu His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 36
<211> LENGTH: 6
<212> TYPE: PRT
<213> ORGANISM: human

<400> SEQUENCE: 36

Ser Leu Gly Ser Arg Ala
1               5

<210> SEQ ID NO 37
<211> LENGTH: 3
<212> TYPE: PRT
<213> ORGANISM: human

<400> SEQUENCE: 37

Asn Asn Gln
1

<210> SEQ ID NO 38
<211> LENGTH: 12
<212> TYPE: PRT
<213> ORGANISM: human

<400> SEQUENCE: 38

His Ile Trp Asp Ser Arg Val Pro Thr Lys Trp Val
1               5                   10

<210> SEQ ID NO 39
<211> LENGTH: 5
<212> TYPE: PRT
<213> ORGANISM: human

<400> SEQUENCE: 39

Asp Tyr Phe Ile His
1               5

<210> SEQ ID NO 40
<211> LENGTH: 17
<212> TYPE: PRT
<213> ORGANISM: human

<400> SEQUENCE: 40

Trp Ile Asn Pro Lys Thr Gly Gln Pro Asn Asn Pro Arg Gln Phe Gln
1               5                   10                  15

Gly

<210> SEQ ID NO 41
<211> LENGTH: 7
<212> TYPE: PRT
<213> ORGANISM: human

<400> SEQUENCE: 41

Gln Arg Ser Asp Tyr Trp Asp
1               5

<210> SEQ ID NO 42
<211> LENGTH: 11
<212> TYPE: PRT
<213> ORGANISM: human

<400> SEQUENCE: 42

His Ser Leu Ile His Gly Asp Arg Asn Asn Tyr
1               5                   10

<210> SEQ ID NO 43
<211> LENGTH: 3
<212> TYPE: PRT
<213> ORGANISM: human

<400> SEQUENCE: 43

Leu Ala Ser
1

<210> SEQ ID NO 44
<211> LENGTH: 11
<212> TYPE: PRT
<213> ORGANISM: human

<400> SEQUENCE: 44

Cys Met Gln Gly Arg Glu Ser Pro Trp Thr Phe
1               5                   10

<210> SEQ ID NO 45
<211> LENGTH: 7
<212> TYPE: PRT
<213> ORGANISM: human

<400> SEQUENCE: 45

Gln Ala Asn Gly Tyr Leu Asn
1               5

```
<210> SEQ ID NO 46
<211> LENGTH: 7
<212> TYPE: PRT
<213> ORGANISM: human

<400> SEQUENCE: 46

Asp Gly Ser Lys Leu Glu Arg
1               5

<210> SEQ ID NO 47
<211> LENGTH: 5
<212> TYPE: PRT
<213> ORGANISM: human

<400> SEQUENCE: 47

Gln Val Tyr Glu Phe
1               5

<210> SEQ ID NO 48
<211> LENGTH: 8
<212> TYPE: PRT
<213> ORGANISM: human

<400> SEQUENCE: 48

Gly Asp Ser Met Asn Asn Tyr Tyr
1               5

<210> SEQ ID NO 49
<211> LENGTH: 7
<212> TYPE: PRT
<213> ORGANISM: human

<400> SEQUENCE: 49

Ile Ser Asp Arg Glu Ser Ala
1               5

<210> SEQ ID NO 50
<211> LENGTH: 26
<212> TYPE: PRT
<213> ORGANISM: human

<400> SEQUENCE: 50

Ala Thr Ala Arg Arg Gly Gln Arg Ile Tyr Gly Val Val Ser Phe Gly
1               5                   10                  15
Glu Phe Phe Tyr Tyr Tyr Ser Met Asp Val
            20                  25

<210> SEQ ID NO 51
<211> LENGTH: 6
<212> TYPE: PRT
<213> ORGANISM: human

<400> SEQUENCE: 51

Ala Leu Gly Ser Arg Ala
1               5

<210> SEQ ID NO 52
<211> LENGTH: 12
<212> TYPE: PRT
<213> ORGANISM: human

<400> SEQUENCE: 52

His Met Trp Asp Ser Arg Ser Gly Phe Ser Trp Ser
```

-continued

```
1               5               10

<210> SEQ ID NO 53
<211> LENGTH: 10
<212> TYPE: PRT
<213> ORGANISM: human

<400> SEQUENCE: 53

Gly Ser Leu Val Gly Asn Trp Asp Val Ile
1               5                   10

<210> SEQ ID NO 54
<211> LENGTH: 5
<212> TYPE: PRT
<213> ORGANISM: artificial sequence
<220> FEATURE:
<223> OTHER INFORMATION: linker sequence

<400> SEQUENCE: 54

Gly Gly Gly Gly Ser
1               5
```